United States Patent
Varani et al.

(10) Patent No.: US 11,148,998 B2
(45) Date of Patent: Oct. 19, 2021

(54) DIMETHYL-NONATETRAENYL-TRIMETHYL-CYCLOHEXYL COMPOUNDS AND USES THEREOF

(71) Applicant: The Regents of the University of Michigan, Ann Arbor, MI (US)

(72) Inventors: James Varani, Ann Arbor, MI (US); Hollis Showalter, Ann Arbor, MI (US); Andy White, Ann Arbor, MI (US); Kent J. Johnson, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 15/987,274

(22) Filed: May 23, 2018

(65) Prior Publication Data
US 2018/0339961 A1 Nov. 29, 2018

Related U.S. Application Data

(60) Provisional application No. 62/510,113, filed on May 23, 2017.

(51) Int. Cl.

| | | |
|---|---|---|
| *A61K 45/06* | (2006.01) | |
| *C07C 235/30* | (2006.01) | |
| *C07D 209/54* | (2006.01) | |
| *C07D 305/06* | (2006.01) | |
| *C07C 233/50* | (2006.01) | |
| *C07C 233/31* | (2006.01) | |
| *C07D 211/74* | (2006.01) | |
| *C07D 207/24* | (2006.01) | |
| *A61P 17/10* | (2006.01) | |
| *A61P 17/06* | (2006.01) | |
| *A61P 35/02* | (2006.01) | |
| *A61P 17/02* | (2006.01) | |

(52) U.S. Cl.
CPC ............ *C07C 235/30* (2013.01); *A61P 17/02* (2018.01); *A61P 17/06* (2018.01); *A61P 17/10* (2018.01); *A61P 35/02* (2018.01); *C07C 233/31* (2013.01); *C07C 233/50* (2013.01); *C07D 207/24* (2013.01); *C07D 209/54* (2013.01); *C07D 211/74* (2013.01); *C07D 305/06* (2013.01); *A61K 45/06* (2013.01); *A61K 2300/00* (2013.01); *C07C 2601/02* (2017.05); *C07C 2601/16* (2017.05)

(58) Field of Classification Search
None
See application file for complete search history.

(56) References Cited

U.S. PATENT DOCUMENTS

| | | | | |
|---|---|---|---|---|
| 3,950,418 A | * | 4/1976 | Bollag .................. | C07C 403/20 554/51 |
| 4,190,594 A | * | 2/1980 | Gander .................. | A61K 8/671 424/59 |
| 4,216,224 A | * | 8/1980 | Yu ......................... | C07C 403/20 514/476 |
| 5,821,254 A | | 10/1998 | Sporn et al. | |
| 5,837,728 A | | 11/1998 | Purcell | |
| 2007/0270472 A1 | | 11/2007 | Beumer et al. | |
| 2012/0238749 A1 | | 9/2012 | Bemis et al. | |
| 2015/0005266 A1 | | 1/2015 | Purcell | |

FOREIGN PATENT DOCUMENTS

| | | |
|---|---|---|
| GB | 1283887 | 8/1972 |
| JP | 2002-293746 | 10/2002 |
| WO | 2005/079774 | 9/2005 |
| WO | 2012/170952 | 12/2012 |

OTHER PUBLICATIONS

Database Registry Chemical Abstracts Service, Columbus, Ohio, Accession No. RN 1349580-55-7, Entered STN: Dec. 6, 2011.*
International Search Report & Written Opinion, International Patent Application No. PCT/US2018/034106, dated Jul. 30, 2018, 10 pages.
Appleyard VCL, et al., "Activity of MDI-301, a novel synthetic retinoid, in xenografts" Anticancer Drugs. 2004;15(10):991-996.
Aslam MN, et al., "MDI 301 suppresses myeloid leukemia cell growth in vitro and in vivo without the toxicity associated with all-trans retinoic acid therapy" Anti-Cancer Drugs 2015, 26:763-773.
Dame MK, et al., "The Gottingen minipig for assessment of retinoid efficacy in the skin: comparison of results from topically treated animals with results from organ-cultured skin" In Vitro Cell. Dev. Biol. Anim. 2009;45(9):551-557.
De Bottom S, et al., "Incidence, Clinical Features, and Outcome of All Trans-Retinoic Acid Syndrome in 413 Cases Newly Diagnosed Acute Promyelocytic Leukemia" Blood. 1998;92(8):2712-2718.
Frankel SR, et al., "The "Retinoic Acid Syndrome" in Acute Promyelocytic Leukemia" Ann Intern Med. 1992;117:292-296.
Lateef H, et al., "All-trans-Retinoic Acid Suppresses Matrix Metalloproteinase Activity and Increases Collagen Synthesis in Diabetic Human Skin in Organ Culture" Am J Pathol. 2004;165:167-174.
Rittie L, et al., "Retinoid-Induced Epidermal Hyperplasia is Mediated by Epidermal Growth Factor Receptor Activiation Via Specific Induction of its Ligands Heparin-Binding egf and Amphiregulin in Human Skin In Vivo" J Invest Dermatol, 2006; 126:732-739.

(Continued)

*Primary Examiner* — Samantha L Shterengarts
(74) *Attorney, Agent, or Firm* — Casimir Jones, S.C.; Robert A. Goetz

(57) ABSTRACT

This invention is in the field of medicinal chemistry. In particular, the invention relates to a new class of small-molecules having a dimethyl-nonatetraenyl-trimethyl-cyclohexyl structure useful as therapeutics for the treatment of subjects suffering from disorders characterized by abnormal proliferation and/or abnormal differentiation of cells, in particular of cells of which the growth and differentiation is sensitive to the actions of retinoids.

16 Claims, 16 Drawing Sheets

(56) References Cited

OTHER PUBLICATIONS

Vahdat L, et al., "Early Mortality and Retinoic Acid Syndrome in Acute Promyelocytic Leukemia: Impact . . ." Blood. 1994;84(11):3843-3849.

Varani J, et al., "Retinoic Acid Stimulation of Human Dermal Fibroblast Proliferation is Dependent on Suboptimal Extracellular CA2+ Concentration" Am. J. Path. 1990; 136:1275-1281.

Varani J, et al., "Inhibition of Epithelial Cell Adhesion by Retinoic Acid" Am. J. Path. 1991; 138:887-895.

Varani J, et al., "Effects of All-Trans Retinoic Acid and Ca++ on Human Skin in Organ Culture" Am J Pathol. Jan. 1993;142(1):189-98.

Varani J, et al., "All-Trans Retinoic Acid and Extracellular Ca2+ Differentially Influence . . . " Am J Pathol. Jun. 1993;142(6)1813-22.

Varani K, et al., "All-Trans Retinoic Acid Inhibits Fluctuations in Intracellular Ca2+ Resulting from Changes in Extracellular Ca2+" Am J. Pathol. 1995, 147:718-729.

Varani J, et al., "All-Trans Retinoic Acid Reduces Membrane Fluidity of Human Dermal Fibroblasts" Amer. J. Pathol. 1996; 148: 1307-1312.

Varani J, et al., "Separation of retinoid-induced epidermal and dermal thickening from skin irritation" Arch. Dermatol. Res. 2003; 295:255-262.

Varani J, et al., "MDI 301, a non-irritating retinoid, induces changes in human skin that underlie repair" Arch. Dermatol. Res. 2007; 298:439-448.

Varani J, et al., "Retinoid-induced epidermal hyperplasia in human skin organ culture: inhibition with soy extract and soy isoflavones" Exp Mol Pathol. 2004;77(3)176-83.

Varani J, et al., "All-trans Retinoic Acid (RA) Stimulates Events in Organ-cultured human skin that underlie repair" J Clin Invest. 1994;94:1747-1756.

Varani J, et al., "All-Trans Retinoic Acid Stimulates Growth of Adult Human Keratinocytes Cultured in Growth Factor-Deficient Medium, Inhibits Producation of Thrombospondin and Fibronectin, and Reduces Adhesion" J. Invest. Dermatol. 1989; 93:449-454.

Varani J, et al., "All-Trans Retinoic Acid Stimulates Growth and Extracellular Matrix Production in Growth-Inhibited Cultured Human Skin Fibroblasts" J. Invest. Dermatol. 1990; 94:717-723.

Varani J, et al., "Induction of Proliferation of Growth-Inhibited Keratinocytes and Fibroblasts . . . " J. Invest. Dermatol. 1991; 97:917-921.

Varani J., et al., "Retinoid Toxicity for Fibroblasts and Epithelial Cells Is Separable From Growth Promoting Activity" J. Invest. Dermatol. 1993; 101:839-842.

Varani J, et al., "Human Skin in Organ Culture and Human Skin Cells (Keratinocytes and Fibroblasts) in Monolayer culture . . . " Toxicol. Pathol. 2007; 35:693-701.

Warner RL, et al., "MDI 301, a nonirritating retinoid, improves abrasion wound healing in damaged/atrophic skin" Wound Repair 2008; Regen. 16:117-124.

EP Search Report, EP Patent Application No. 18806688.0, dated Feb. 10, 2021, 9 pages.

Magoulas G et al. "Preparation of spermine conjugates with acidic retinoids with potent ribonuclease P inhibitory activity" EP Journal of Medicinal Chemistry, Elsevier, Amsterdam, NL, vol. 44, No. 6, Jun. 1, 2009, pp. 2689-2695.

\* cited by examiner

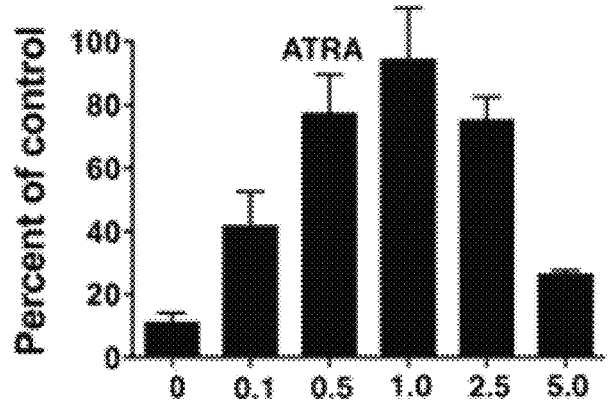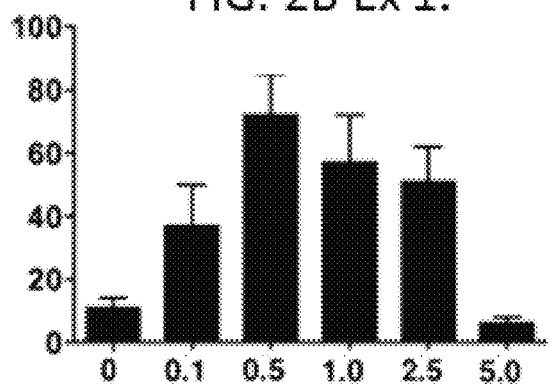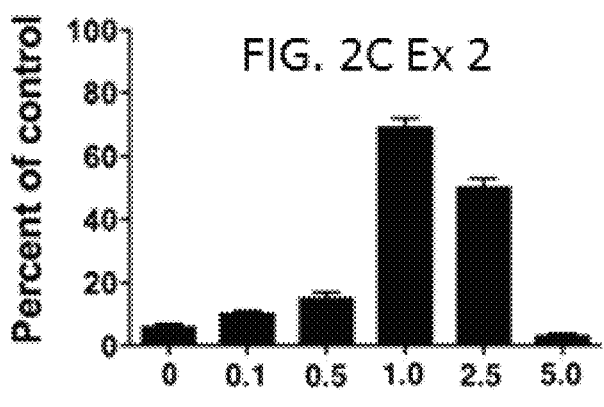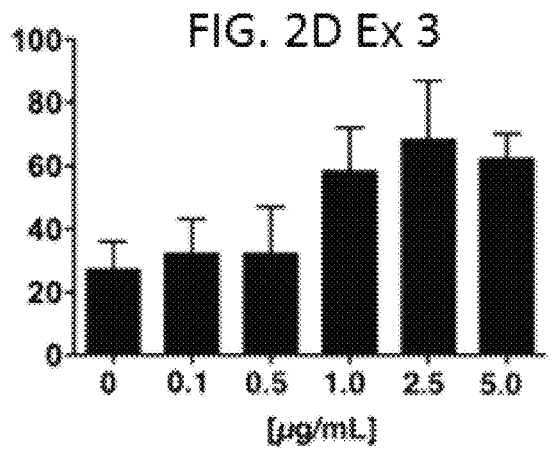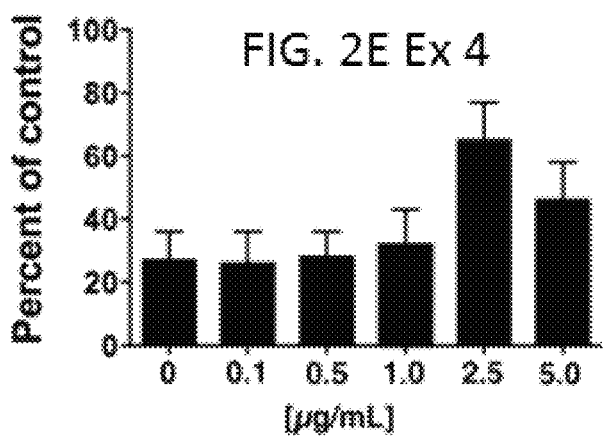

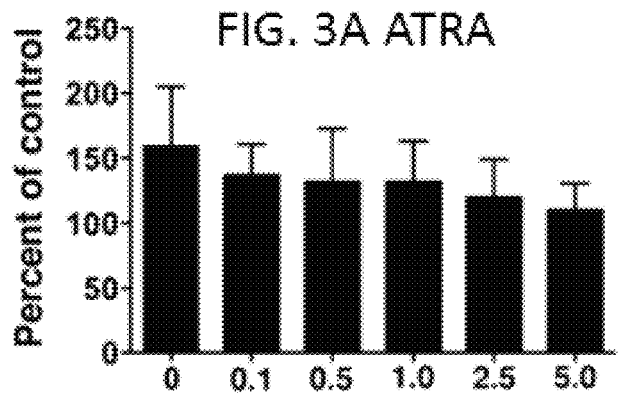
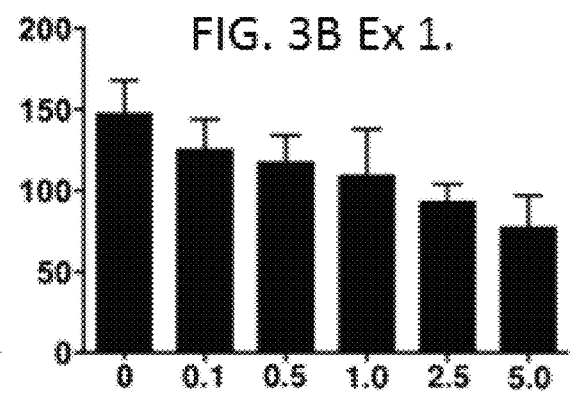
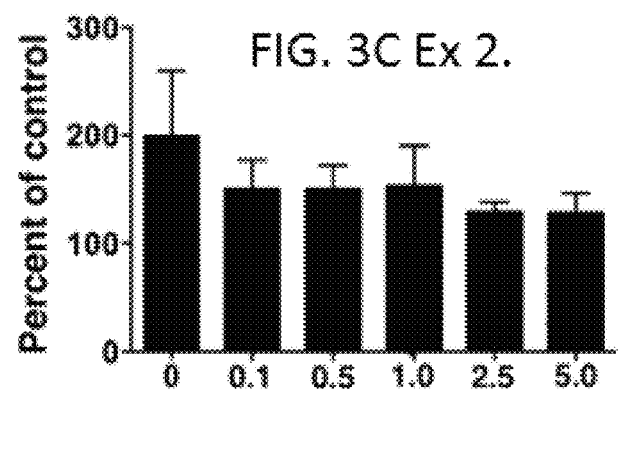
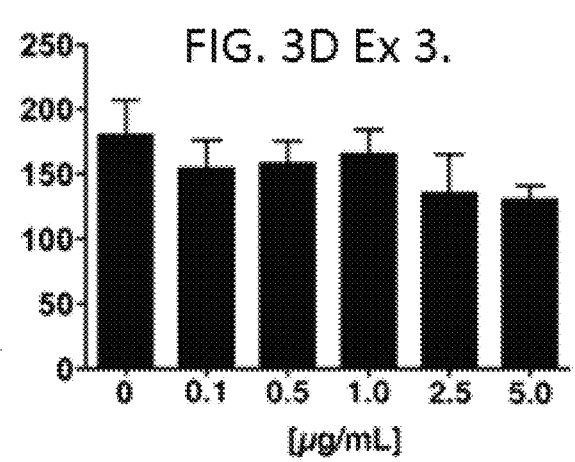
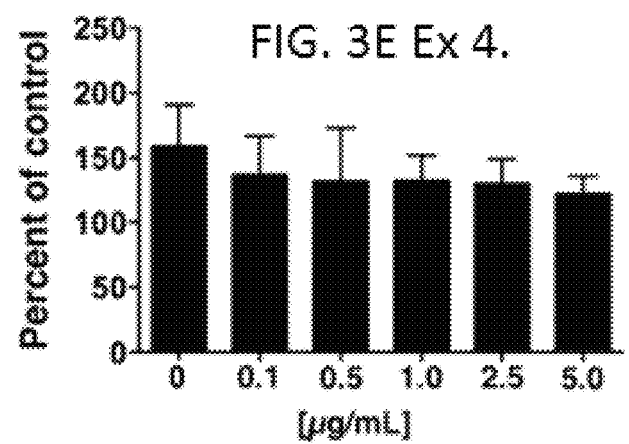

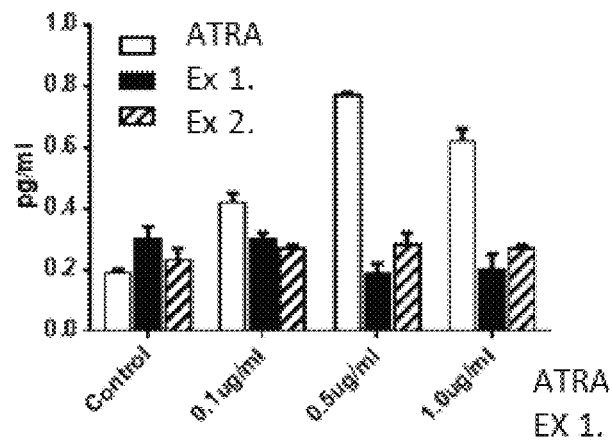
FIG. 4A IL-1β
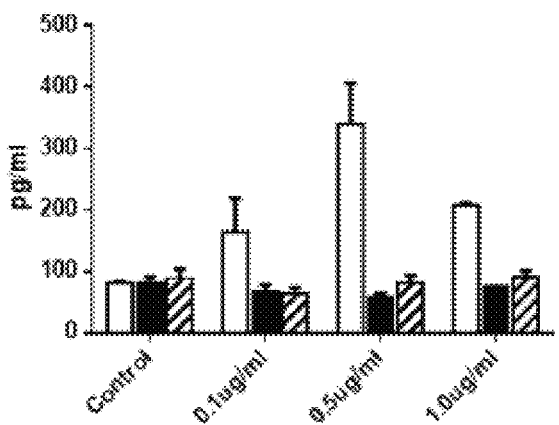
FIG. 4B IL-6
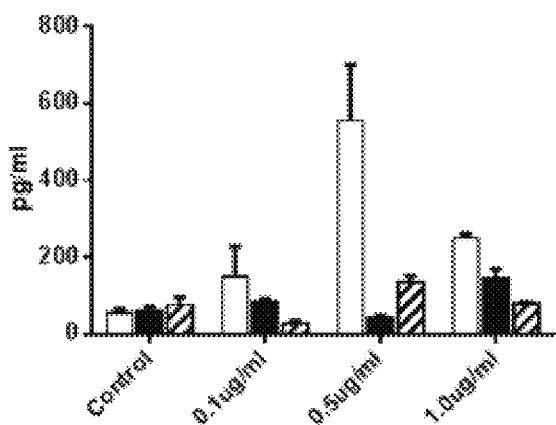
FIG. 4C CXCL4
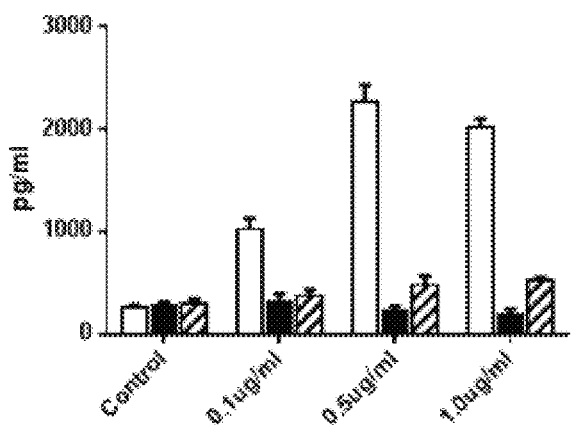
FIG. 4D MCP-1
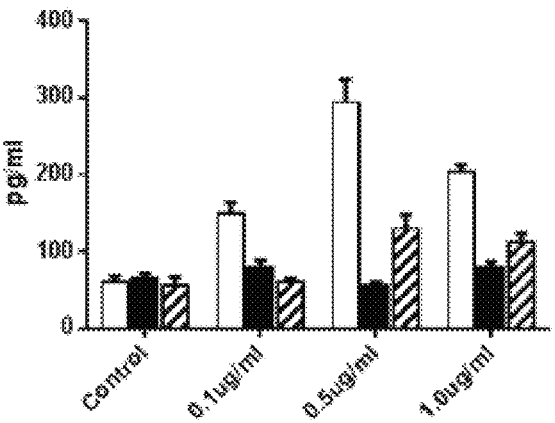
FIG. 4E IL-8

FIG. 10A
FIG. 10B
FIG. 10C
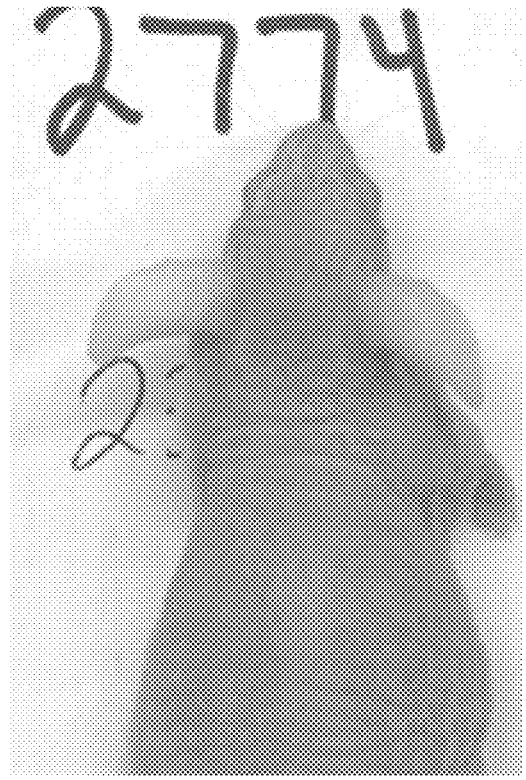

FIG. 15A        L                              R
FIG. 15B        L                              R
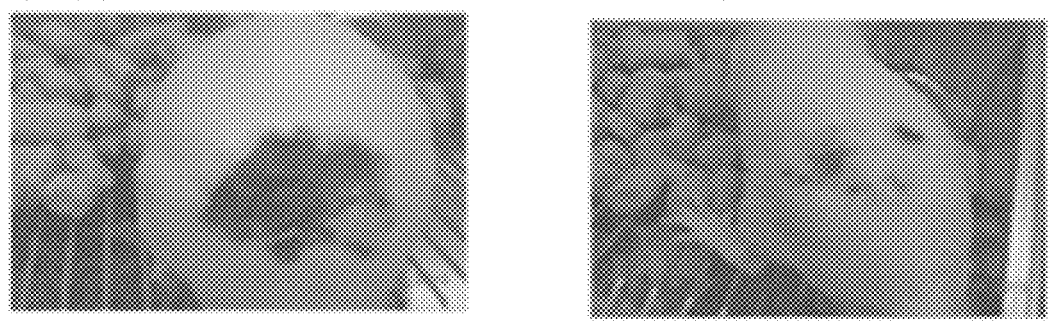
FIG. 15C        L                              R
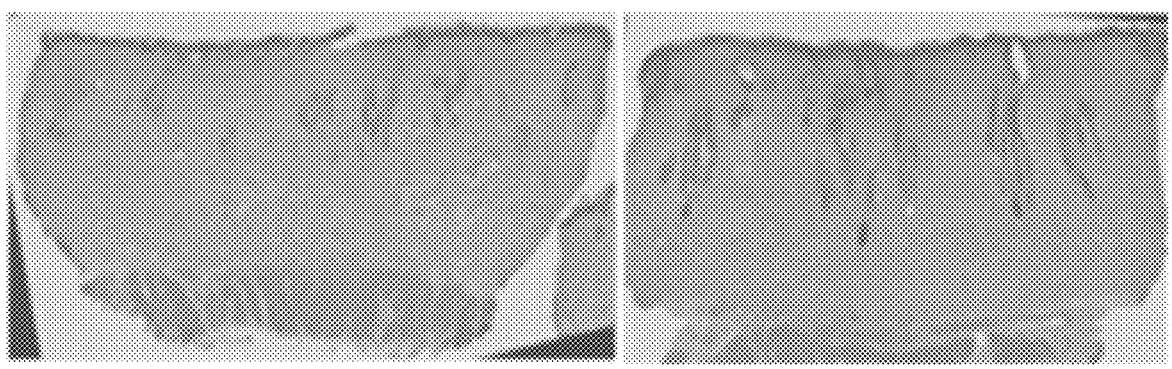

MDI-301

DIMETHYL-NONATETRAENYL-TRIMETHYL-CYCLOHEXYL COMPOUNDS AND USES THEREOF

CROSS-REFERENCE TO RELATED APPLICATIONS

This application claims priority to Provisional Patent Application 62/510,113, filed May 23, 2017, which is herein incorporated by reference in its entirety.

FIELD OF THE INVENTION

This invention is in the field of medicinal chemistry. In particular, the invention relates to a new class of small-molecules having a dimethyl-nonatetraenyl-trimethyl-cyclohexyl structure useful as therapeutics for the treatment of subjects suffering from disorders characterized by abnormal proliferation and/or abnormal differentiation of cells, in particular of cells of which the growth and differentiation is sensitive to the actions of retinoids.

INTRODUCTION

In humans, the skin weighs an average of four kilograms, covers an area of two square meters, and is made of three distinct layers: the epidermis, dermis and subcutaneous tissue. The two main types of human skin are: glabrous skin—i.e., the hairless skin on the palms and soles (also referred to as the "palmoplantar" surfaces),—and hair-bearing skin. Within the latter type, the hairs occur in structures called pilosebaceous units, each with hair follicle, sebaceous gland, and associated arrector pili muscle. The major function of this system is as a barrier against the external environment. The two major cell types that make up the skin include the epidermal keratinocytes (i.e., the epithelial cells that form the outer multicellular layer) and the dermal fibroblasts (i.e., the cells that form the connective tissue of the skin). Both types of cells are sensitive to the biologically active retinoids.

Numerous conditions and/or diseases affect the human integumentary system. Among the most common conditions are inflammatory and keratinization disorders (for example, acne, psoriasis, rosacea, lamellar ichthyosis, epidermolytic hyperkeratosis, Darier's disease, *pityriasis rubra* pilaris, congenital ichthyosiform erythroderma, hyperkeratosis palmaris et plantaris, melasma, plantar warts, callosities, acanthosis *nigricans*, lichen planus, molluscum, melasma, geographic tongue, Fox-Fordyce disease and similar disorders.

The skin is also susceptible to conditions that lead to its breakdown. The chronological aging process is a prime example. As the skin ages, it becomes thinner and more prone to erosions. Exposure to solar radiation (photodamage), chronic steroid use, diabetes and other metabolic or vascular diseases also contribute to skin breakdown. Among the cosmetic consequences are wrinkles and dispigmentation. More serious consequences include easy bruising, increased susceptibility to wounding and poor healing of wounds when they occur. The biologically active retinoids (the subject of this patent) are used in treatment of inflammatory diseases and in the treatment/prevention of skin breakdown.

The biologically active retinoids are also used in the field of oncology. For example, acute promyelocytic leukemia (APL) is treated with all-trans retinoic acid (ATRA) as a first-line therapy. Neuroblastoma is treated with 13-cis retinoic acid. In addition, several other cancer types including head- and neck cancer, lung cancer, breast cancer, uterine cervix cancer, gastrointestinal tract cancer, skin cancer, bladder cancer, prostate cancer and similar disorders have demonstrated retinoid sensitivity.

ATRA is a medication used for the treatment of inflammatory skin diseases (e.g., acne) and for skin repair (e.g., wrinkling). It is also used to treat cancer (e.g., APL). For acne and for skin repair, it is typically applied to the skin as a cream or ointment. In a severe form of acne (nodular-cystic acne), 13-cis retinoic acid is used systemically (taken orally). For leukemia ATRA is used; it may be taken by mouth for up to three months. Topical ATRA is only for use on skin and it should not be applied to eyes or mucosal tissues. Common side effects include skin irritation, redness, swelling, and blistering. In addition, skin is more susceptible to sunburn.

Indeed, current use of retinoids such as ATRA is limited by toxicity manifested as skin irritation when used topically in dermatological conditions and with widespread toxicity (retinoic acid syndrome/differentiation syndrome) when used systemically to treat cancer. Such retinoid-induced skin irritation and systemic toxicity are thought to be a reflection of retinoid capacity to elicit a cytokine storm.

New compounds having the efficacy of currently used retinoids (e.g., ATRA) but without their capacity to induce widespread cytokine generation are needed.

The present invention addresses this need.

SUMMARY OF THE INVENTION

Experiments conducted during the course of the present invention indicate that dimethyl-nonatetraenyl-trimethyl-cyclohexyl compounds described herein have similar activity to ATRA in assays that predict anti-acne efficacy (keratinocyte detachment assay and epidermal thickening assay) and in assays that predict skin-repair efficacy (increased fibroblast survival and epidermal thickening). At the same time, the lack of cytokine generation with such compounds indicate that such compounds will, unlike ATRA, not cause the skin irritation response that is the classic result of topical ATRA use.

Accordingly, the present invention contemplates that exposure of animals (e.g., humans) suffering from disorders characterized by abnormal proliferation and/or abnormal differentiation of cells (e.g., cells of which the growth and differentiation is sensitive to the actions of retinoids) to therapeutically effective amounts of drug(s) having a dimethyl-nonatetraenyl-trimethyl-cyclohexyl structure (that mimic the activity of ATRA without related skin irritation) will produce efficacious responses similar to those of ATRA but without it's side effects.

The present invention contemplates that the dimethyl-nonatetraenyl-trimethyl-cyclohexyl compounds of the present invention satisfy an unmet need for the treatment of disorders situated in the field of oncology, for example, APL, neuroblastoma, head- and neck cancer, lung cancer, breast cancer, uterine cervix cancer, gastrointestinal tract cancer, skin cancer, bladder cancer and prostate cancer and similar disorders.

The present invention contemplates that the dimethyl-nonatetraenyl-trimethyl-cyclohexyl compounds of the present invention satisfy an unmet need for the treatment of disorders situated in the field of dermatology (e.g., inflammatory/keratinizing disorders and disorders related to skin damage, etc.). Examples of such disorders include, but are not limited to rosacea, acne, psoriasis, severe psoriasis, lamellar ichthyosis, plantar warts, callosities, acanthosis *nigricans*, lichen planus, molluscum, melasma, corneal epithelial abrasion, geographic tongue, Fox-Fordyce disease, cutaneous metastatic melanoma and keloids, epidermolytic hyperkeratosis, Darier's disease, *pityriasis rubra* pilaris, congenital ichthyosiform erythroderma, hyperkeratosis palmaris et plantaris, melisma and hyperpigmentation. Disorders related to skin damage include skin made atrophic by aging, photodamaged skin, skin damage related to metabolic diseases such as diabetes, skin damage related to steroid use, and similar disorders.

The present invention contemplates that the dimethyl-nonatetraenyl-trimethyl-cyclohexyl compounds of the present invention satisfy an unmet need for the treatment of such disorders either when administered as monotherapy, or when administered in a temporal relationship with additional agent(s), such as other pharmaceutical agents known to be useful in treating such disorders (combination therapies). In certain embodiments of the invention, combination treatment of animals with a therapeutically effective amount of a compound of the present invention and a course of an additional pharmaceutical agent useful in treating such disorders produces a greater response and clinical benefit in such animals compared to those treated with the compound or additional agent alone. Since the doses for all approved drugs are known, the present invention contemplates the various combinations of them with the present compounds.

Indeed, the Applicants have found that certain dimethyl-nonatetraenyl-trimethyl-cyclohexyl compounds serve as therapeutics for the treatment of disorders in the field of oncology, for example, APL, neuroblastoma, head- and neck cancer, lung cancer, breast cancer, uterine cervix cancer, gastrointestinal tract cancer, skin cancer, bladder cancer and prostate cancer and similar disorders; and in the field of dermatology, for example, inflammatory/keratinization disorders such as rosacea, acne, psoriasis, severe psoriasis, lamellar ichthyosis, plantar warts, callosities, acanthosis *nigricans*, lichen planus, molluscum, melisma, corneal epithelial abrasion, geographic tongue, Fox-Fordyce disease, cutaneous metastatic melanoma and keloids, epidermolytic hyperkeratosis, Darier's disease, *pityriasis rubra* pilaris, congenital ichthyosiform erythroderma, hyperkeratosis palmaris et plantaris, melasma, hyperpigmentation and similar disorders. Certain dimethyl-nonatetraenyl-trimethyl-cyclohexyl compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

As such, the present invention provides a new class of small-molecules having a dimethyl-nonatetraenyl-trimethyl-cyclohexyl structure useful as therapeutics for the treatment of skin conditions within the fields of, for example, oncology and dermatology.

In a particular embodiment, dimethyl-nonatetraenyl-trimethyl-cyclohexyl compounds encompassed within Formula I are provided:

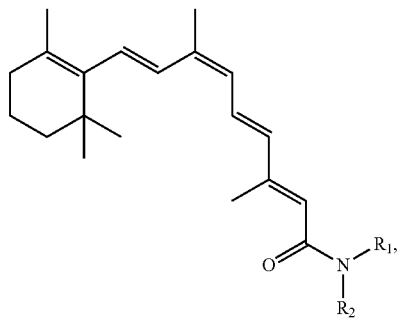

including pharmaceutically acceptable salts, solvates, and/or prodrugs thereof.

In some embodiments, $R_1$ is $CH_3$, $CF_3$, or an optionally substituted saturated or unsaturated alkyl chain moiety having two or more carbon molecules.

In some embodiments, $R_1$ is $CH_3$, $CF_3$, or $C_{2-4}$ alkyl.

In some embodiments, $R_1$ is $CH_3$, $CF_3$, or is a straight or branched carbon chain of 1-10 carbon atoms, which can contain up to two double or triple bonds, as allowed by valency, and can be optionally substituted with up to three substituents.

In some embodiments wherein the $R_1$ moiety is optionally substituted, such a $R_1$ moiety is optionally substituted with a saturated or unsaturated alkyl chain, a saturated or unsaturated cycloalkyl moiety, a saturated or unsaturated branched-alkyl moiety, a halogen (e.g., chlorine, fluorine, bromine, iodine), an optionally substituted cyano-moiety, an optionally substituted oxo-moiety (e.g., =O), or

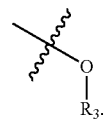

In some embodiments, $R_2$ is

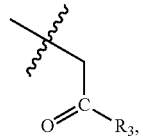

$CH_3$, $CF_3$, or an optionally substituted saturated or unsaturated alkyl chain moiety having two or more carbon molecules.

In some embodiments, $R_2$ is $CH_3$, $CF_3$, or is a straight or branched carbon chain of 1-10 carbon atoms, which can contain up to two double or triple bonds, as allowed by valency, which can be optionally substituted with up to three substituents.

In some embodiments wherein the $R_2$ moiety is optionally substituted, such a $R_2$ moiety is optionally substituted with a saturated or unsaturated alkyl chain, a saturated or unsaturated cycloalkyl moiety, a saturated or unsaturated branched-alkyl moiety, a halogen e.g., chlorine, fluorine, bromine, iodine), an optionally substituted cyano-moiety, an optionally substituted oxo-moiety (e.g., =O), CH$_2$(CO)R$_3$, or

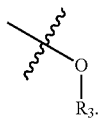

In some embodiments,

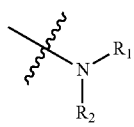

form an optionally substituted cyclic moiety having from 4-7 carbon atoms, optionally substituted with up to three groups chosen independently C$_{1-10}$ alkyl, C$_{3-10}$ alkenyl, C$_{3-10}$ alkynyl, all of which may be straight chain or branched C$_{3-10}$ cycloalkyl, C$_{2-5}$ spiroalkyl, halogen, cyano, oxo, CF$_3$ or OR$_3$, such that when R$_3$ is bonded directly to oxygen, it is R$_4$.

In some embodiments, such an

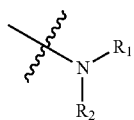

moiety formed as an optionally substituted cyclic moiety having from 4-7 carbon atoms is selected from

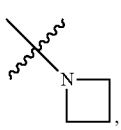

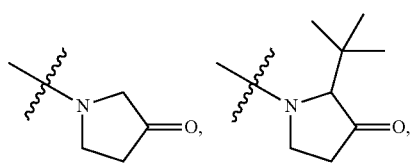

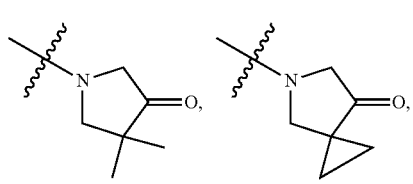

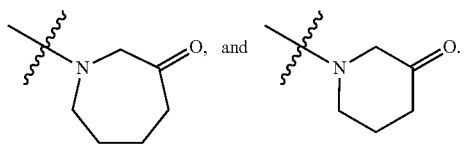

In some embodiments, R1 and R2 are different.

In some embodiments, R$_3$ is an optionally substituted saturated or unsaturated alkyl chain moiety having two or more carbon molecules.

In some embodiments, R$_3$ is

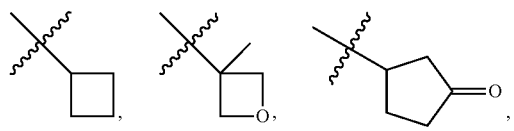

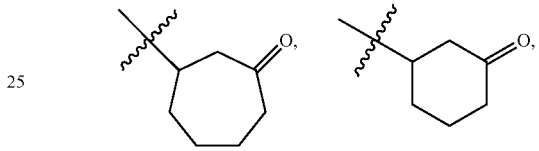

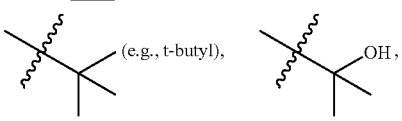

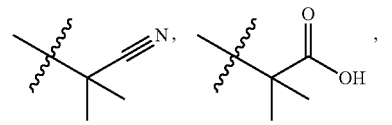

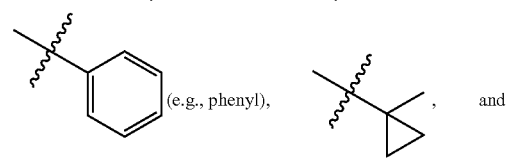

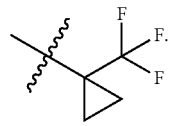

In some embodiments R$_1$ and R$_2$, along with the nitrogen both are bonded to can form a ring having 4-7 atoms, optionally substituted with up to three groups chosen independently C$_{1-10}$ alkyl, C$_{3-10}$ alkenyl, C$_{3-10}$ alkynyl, all of which may be straight chain or branched C$_{3-10}$ cycloalkyl, C$_{2-5}$ spiroalkyl, halogen, cyano, oxo, CF$_3$ or OR$_3$, such that when R$_3$ is bonded directly to oxygen, it is R$_4$.

In some embodiments, R$_3$ is C$_{2-10}$ alkyl, C$_{2-10}$ alkenyl, C$_{2-10}$ alkynyl, all of which may be straight chain or branched, phenyl, monocyclic or bicyclic 5-10 membered heteroaryl containing up to four heteroatoms chosen from N, O and S, C$_{3-7}$ cycloalkyl, 4-7 membered heterocycloalkyl, optionally substituted with up to three groups chosen independently from C$_{1-10}$ alkyl, C$_{3-10}$ cycloalkyl, C$_{2-10}$ alkenyl C$_{3-10}$ cycloalkenyl, C$_{2-10}$ alkynyl, C$_{3-10}$ branched alkyl, C$_{3-10}$ branched alkenyl, C$_{4-10}$ branched alkynyl, C$_{2-5}$ spiroalkyl, halogen, hydroxy, carboxy, cyano, oxo, or CF$_3$.

In some embodiments, $R_4$ is $C_{1-4}$ lower alkyl straight chain or branched, $C_{3-4}$, alkenyl straight chain or branched, $C_{3-4}$ alkynyl, $C_{2-4}$ lower acyl, $CF_3$ or $C_2$ fluoroalkyl.

In some embodiments, $R_4$ is $C_{1-4}$ alkyl.

In certain embodiments, the compounds of Formula 1 described immediately above can have $R_1$ or $R_2$ or $R_3$ each with up to three substituents are independently chosen from, $C_{3-8}$ cycloalkyl, $C_{4-8}$ cycloalkenyl, halo, CN, $N_3$, $CF_3$, $NO_2$, cycloalkyl, substituted cycloalkyl, cycloalkenyl substituted cycloalkenyl, heterocycloalkyl, phenyl, substituted phenyl, heteroaryl, substituted heteroaryl, hydroxy, oxo, thio, thiono, amino, cyano, $C_{1-6}$ alkoxy, $C_{3-6}$ cycloalkoxy, $C_{1-6}$alkylthio, $C_{3-6}$ cycloalkylthio, $C_{1-6}$ alkylsulfonyl, $C_{3-6}$ cycloalkylsulfonyl, monoalkylamino, dialkylamino, monocycloalkylamino, or bis(cycloalkyl)amino.

In some embodiments of the compounds of Formula I described immediately above $R_1$ is $CH_3$, $CF_3$, $C_{2-10}$ alkyl, $C_{3-10}$ alkenyl, $C_{3-10}$ alkynyl, all of which may be straight chain or branched, or $CF_3$, which can be optionally substituted with up to three groups chosen independently from $C_{1-10}$ alkyl, $C_{3-10}$ cycloalkyl, $C_{2-10}$ alkenyl $C_{3-10}$ cycloalkenyl, $C_{2-10}$ alkynyl, wherein all aliphatics may be straight chain or branched, halogen, hydroxy, cyano, oxo, $CF_3$ or $OR_3$, such that when $R_3$ is bonded directly to oxygen, it is $R_4$; and independently $R_2$ is $C_{1-10}$ alkyl, $C_{3-10}$ alkenyl, $C_{3-10}$ alkynyl, all of which may be straight chain or branched, or $CF_3$, which can be optionally substituted with up to three groups chosen independently from $C_{1-10}$ alkyl, $C_{3-10}$ cycloalkyl, $C_{2-10}$ alkenyl $C_{3-10}$ cycloalkenyl, $C_{2-10}$ alkynyl, wherein all aliphatics may be straight chain or branched, halogen, hydroxy, cyano, oxo, $CF_3$ or $OR_3$, such that when $R_3$ is bonded directly to oxygen, it is $R_4$.

In some embodiments, the following compounds are contemplated for Formula I:

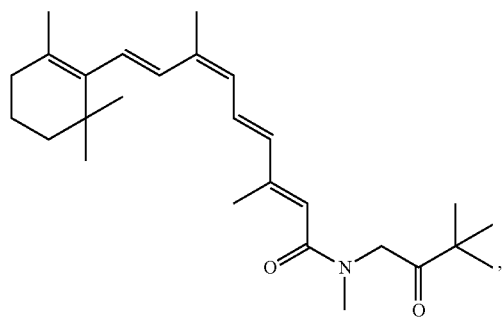

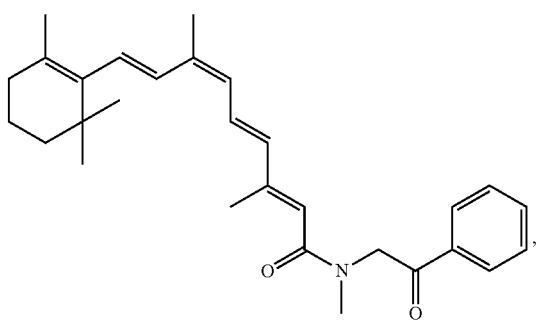

-continued

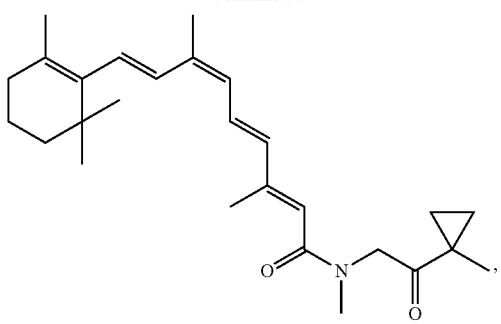

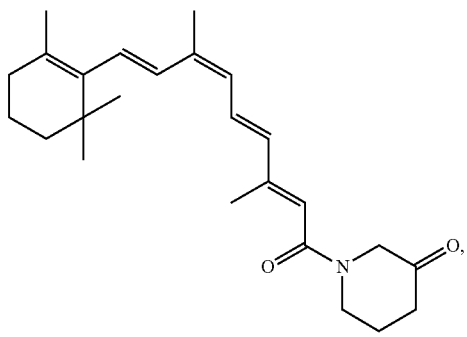

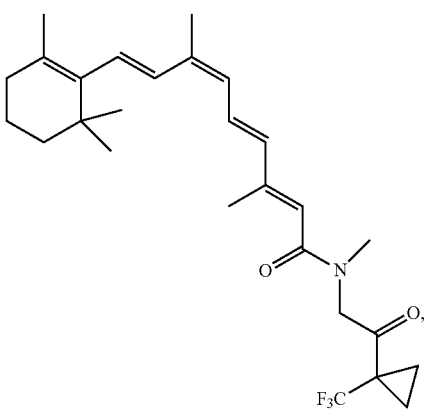

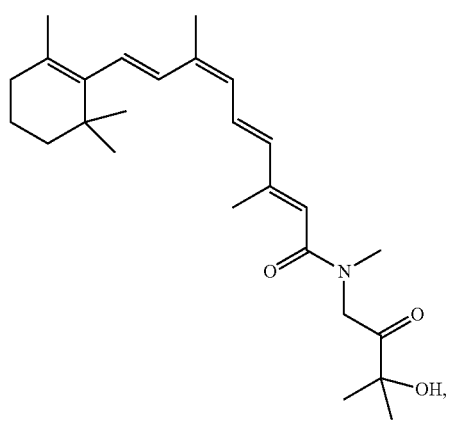

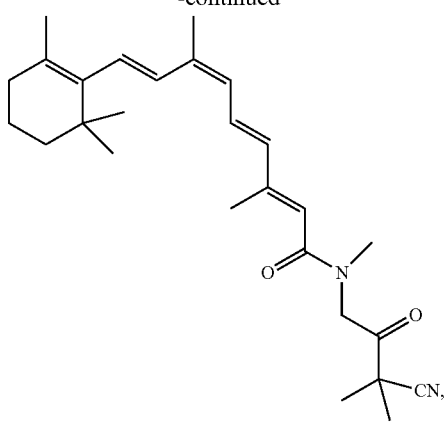
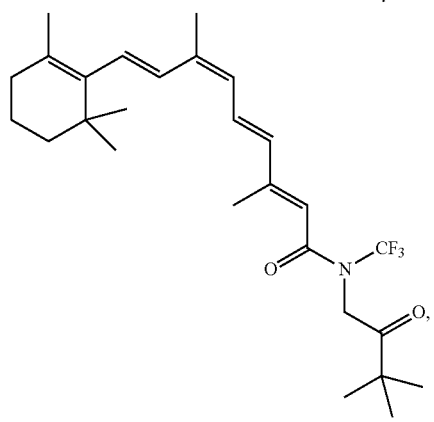
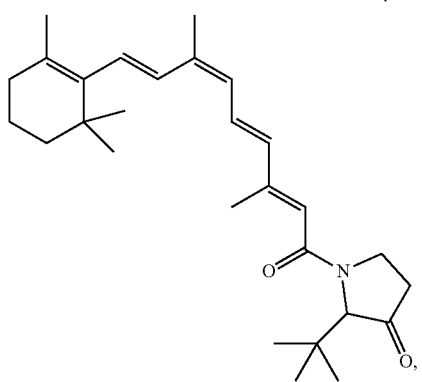
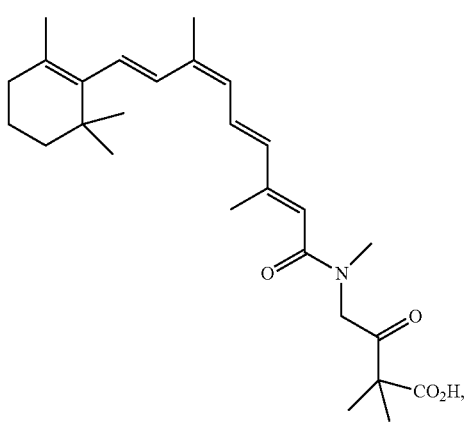

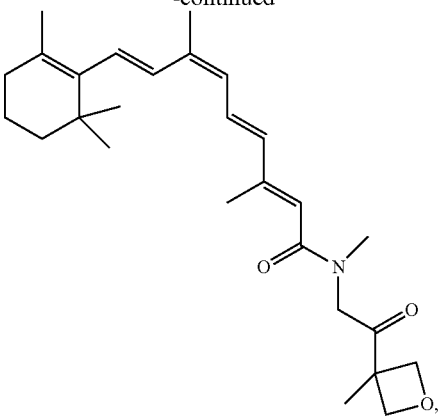
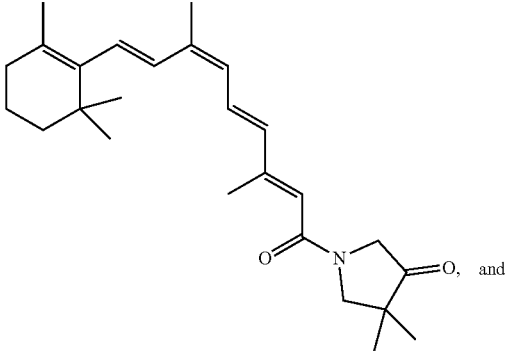
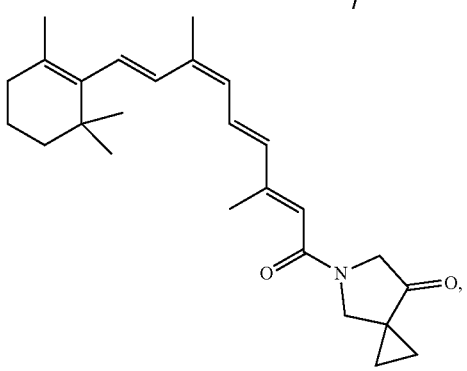

or a pharmaceutically acceptable salt, solvate, or prodrug thereof.

The invention also provides pharmaceutical compositions comprising the compounds of the invention in a pharmaceutically acceptable carrier.

The invention further provides processes for preparing any of the compounds of the present invention through following at least a portion of the techniques recited the Examples.

In certain embodiments, the dimethyl-nonatetraenyl-trimethyl-cyclohexyl compounds are useful in the treatment and/or the prevention of disorders characterized by abnormal proliferation and/or abnormal differentiation of cells, in particular of cells of which the growth and differentiation is sensitive to the actions of retinoids. Such disorders are situated in the field of oncology, for example, APL, neuroblastoma, head- and neck cancer, lung cancer, breast cancer, uterine cervix cancer, gastrointestinal tract cancer, skin cancer, bladder cancer and prostate cancer and similar disorders; and in the field of dermatology, for example, inflammatory/keratinization disorders such as rosacea, acne, psoriasis, severe psoriasis, lamellar ichthyosis, plantar warts, callosities, acanthosis *nigricans*, lichen planus, molluscum, melasma, corneal epithelial abrasion, geographic tongue, Fox-Fordyce disease, cutaneous metastatic melanoma and keloids, epidermolytic hyperkeratosis, Darier's disease, *pityriasis rubra* pilaris, congenital ichthyosiform erythroderma, hyperkeratosis palmaris et plantaris, melisma, hyperpigmentation and similar disorders.

In view of the above described uses of the dimethyl-nonatetraenyl-trimethyl-cyclohexyl compounds, it follows that the present invention provides a method of treating warm-blooded animals suffering from diseases which are characterized by an abnormal proliferation and/or abnormal differentiation of normal, preneoplastic or neoplastic cells, whether they are epithelial or mesenchymal; whether they are of ectodermal, endodermal or mesodermal origin. Said method comprises the systemic or topical administration of an amount of a dimethyl-nonatetraenyl-trimethyl-cyclohexyl compound described herein effective in treating the above described disorders, in particular oncology disorders and keratinization disorders, optionally in the presence of an effective amount of an additional therapeutic agent known to be effective in treating the specific disorder.

As noted, the dimethyl-nonatetraenyl-trimethyl-cyclohexyl compounds described herein may conveniently be used in combination with a chemotherapeutic agent, in particular an anti-neoplastic agent such as, e.g. daunorubicin, doxorubicin, vincristine, vinblastine, etoposide, taxol, taxotere, dactinomycin, mitoxantrone, mitomycin, trimetrexate and the like. The combination may be administered separately, simultaneously, concurrently or consecutively, or the combination may also be presented in the form of one pharmaceutical formulation. Thus, the present invention also involves a pharmaceutical product comprising (a) a compound described herein and (b) a chemotherapeutic agent, as a combined preparation for simultaneous, separate or sequential use in the therapeutic or prophylactic treatment of warm-blooded animals suffering from disorders characterized by abnormal proliferation and/or abnormal differentiation of cells. The invention also provides pharmaceutical compositions comprising the compounds of the invention in a pharmaceutically acceptable carrier.

The present invention also provides kits comprising a compound of the invention and instructions for administering the compound to an animal. The kits may optionally contain other therapeutic agents. Such a product may comprise a kit comprising a container containing a pharmaceutical composition of a compound described herein, and another container comprising a pharmaceutical composition of the chemotherapeutic agent. The product with separate compositions of the two active ingredients has the advantage that appropriate amounts of each component, and timing and sequence of administration can be selected in function of the patient. The present invention further concerns a method of treating patients suffering from disorders characterized by abnormal proliferation and/or abnormal differentiation of cells, said method consisting of administering to a patient (a) an effective amount of a compound described herein and (b) an effective amount of a chemotherapeutic agent.

Additional embodiments are described herein.

BRIEF DESCRIPTION OF DRAWINGS

FIGS. 2A-2E: Fibroblast survival under low-calcium conditions: Comparison of all-trans retinoic acid (ATRA) FIG. 2A, with four novel retinoids (Examples 1, 2, 3 and 4 FIGS. 2B-2E respectively with control (0 µg/mL in each panel). Values shown are means and standard deviations based on n=6 separate date points for each compound. This figure shows that all four of these retinoids are, like ATRA, capable of protecting fibroblasts from lysis under low-calcium conditions. Ex. 1 indicates that it is as effective as ATRA.

FIGS. 3A-3E: Retinoid-induced fibroblast toxicity: Comparison of all-trans retinoic acid (ATRA) FIG. 3A, with four novel retinoids (Examples 1, 2, 3 and 4 FIGS. 3B-3E respectively with control (0 µg/mL in each panel). Values shown are means and standard deviations based on n=6 separate date points for each compound. This figure shows that all four of these retinoids are similar to ATRA in their lack of fibroblast cytotoxicity at concentrations as high as 5 µg/mL.

FIGS. 4A-4E: Comparison of Examples 1 & 2 with ATRA for induction of pro-inflammatory cytokines IL1β (4A) IL-6 (4B), CXCL4 (4C) MCP-1 (4D) and IL-8 (4E). Fibroblasts were grown in KBM supplemented with 1.5 mM calcium (i.e., as in the fibroblast cytotoxicity assay) for two days. Culture fluids obtained at the end of the incubation period were assessed for several pro-inflammatory cytokines using a multiplex (ELISA-type) assay. Values shown are means and ranges based on duplicate samples in a single experiment. The experiment was repeated two times with similar results. Thus, with the two novel retinoids, Examples 1 & 2, there was no evidence of cytokine induction at the highest concentration—a concentration that supported fibroblast survival (FIG. 2) and was not cytotoxic (FIG. 3).

FIG. 8B shows NB4 cells after exposure to Compound 2 (50 µg/mL) for 48 hours in the same culture medium.

FIGS. 10A-C: Lack of Dose-related skin irritation after 21 day topical treatment of rhino mice with 100 µL DMSO control (10A) and 100 µL DMSO containing Example 2 at 0.1 (10B) and 0.3% concentrations (10C).

FIG. 12A shows rhino mouse skin treated with DMSO for 21 days, and shows both the thin dermis and large utriculi typical of this mouse, and is essentially identical to that expected for untreated rhinomouse skin. FIG. 12B shows the rhino mouse skin treated with 0.1% ATRA for 21 days. Although the overall dermal layer is considerably thicker, and the utriculi have gone, the dermal layer has large necrotic areas, and is heavily infiltrated with activated leukocytes and macrophages. FIG. 12C shows skin treated topically with Example 2 at 0.3%, and shows both a considerably thickened dermis and a loss of the utriculi, but without any necrosis or infiltration of activated immune system cells.

FIG. 13A shows rhino mouse skin treated with DMSO for 21 days, and shows both the thin dermis and large utriculi typical of this mouse. FIG. 13B shows rhino mouse skin treated topically for 21 days with 0.1% Example 2, and shows normalization of dermal thickness, but still many structural remnants of utriculi. Example 13C picture shows rhino mouse skin treated topically for 21 days with 0.3% Example 2, and also shows normalization of dermal thickness, but here there is no residual trace of utriculi.

FIGS. 15A-C: Results from a study in rats in which the skin was made atrophic by topical steroid treatment and then wounded. Panel 15AL shows wound appearances at timezero in a control animal versus one treated with MDI-301 (1%) 15AR. Panel B shows the degree of healing in a control animal (15BL) versus one treated with MDI-301 (1%) (15BR) after 13 days. Panel C shows histology of the wound sites. In the control animal (15CL), there was incomplete re-epithelialization over the wound and little collagen deposition in the dermis. By comparison, in the MDI 301 treated rat (15CR), there was a confluent layer of epithelial keratinocytes over the wound site and a pronounced zone of fibroblast proliferation with new collagen formation under the epithelial layer. Note the lack of skin irritation (15BR) and lack of inflammation (15CR) animals. The lack of irritation/inflammation is expected in the control animal but is unusual for a retinoid-treated animal. The data shown here was consistent over n=5 animals per group.

DEFINITIONS

Figure 1:
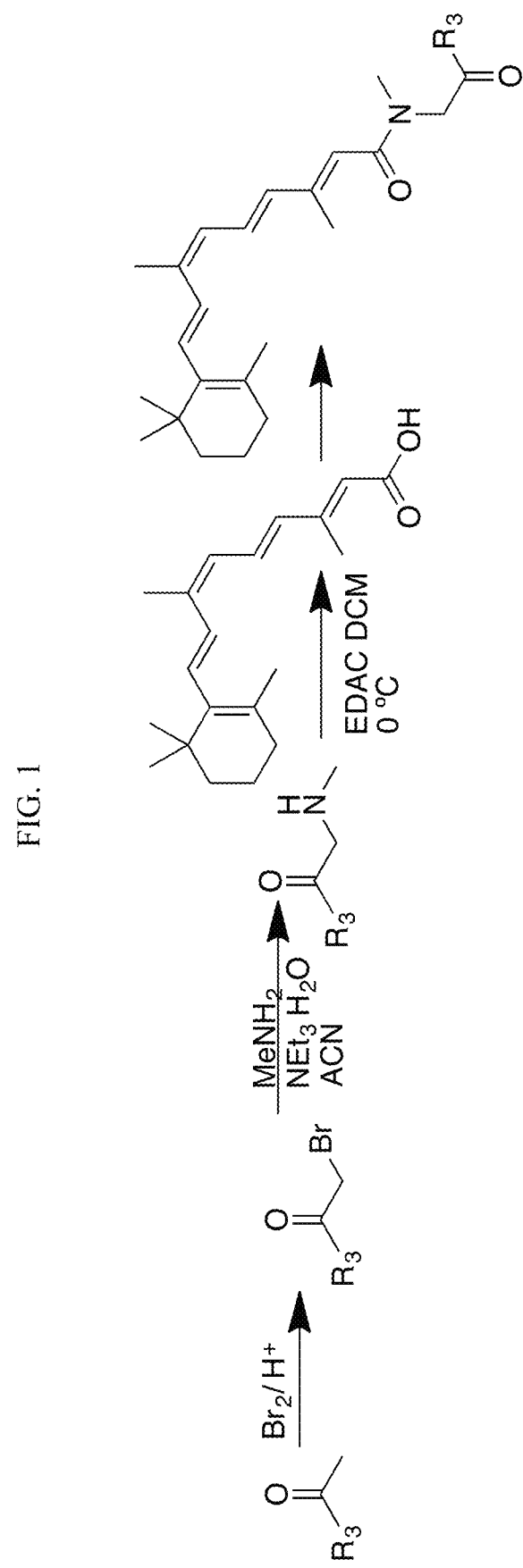
FIG. 1: Synthetic scheme for certain preferred compounds of the invention.

The term "anticancer agent" as used herein, refer to any therapeutic agents (e.g., chemotherapeutic compounds and/or molecular therapeutic compounds), antisense therapies, radiation therapies, or surgical interventions, used in the treatment of hyperproliferative diseases such as cancer (e.g., in mammals, e.g., in humans).

The term "prodrug" as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, water solubility, toxicity, lack of specificity, or limited bioavailability. Exemplary prodrugs comprise an active drug molecule itself and a chemical masking group (e.g., a group that reversibly suppresses the activity of the drug). Some prodrugs are variations or derivatives of compounds that have groups cleavable under metabolic conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of water solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol) or esters prepared by reaction of parent alcohol with a suitable carboxylic acid, (e.g., an amino acid), amides prepared by reaction of the parent acid compound with an amine, basic groups reacted to form an acylated base derivative (e.g., a lower alkylamide), or phosphorus-containing derivatives, e.g., phosphate, phosphonate, and phosphoramidate esters, including cyclic phosphate, phosphonate, and phosphoramidate (see, e.g., U.S. Patent Application Publication No. U.S. 2007/0249564 A1; herein incorporated by reference in its entirety).

The term "pharmaceutically acceptable salt" as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "solvate" as used herein, refers to the physical association of a compound of the invention with one or more solvent molecules, whether organic or inorganic. This physical association often includes hydrogen bonding. In certain instances, the solvate is capable of isolation, for example, when one or more solvate molecules are incorporated in the crystal lattice of the crystalline solid. "Solvate" encompasses both solution-phase and insoluble solvates. Exemplary solvates include hydrates, ethanolates, and methanolates.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, in one embodiment, a therapeutically effective amount will refer to the amount of a therapeutic agent that decreases the rate of tumor growth, decreases tumor mass, decreases the number of metastases, increases time to tumor progression, or increases survival time by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, Pa., 19th ed. 1995. As used herein the term "aliphatic" encompasses the terms alkyl, alkenyl, alkynyl. Unless otherwise stated, aliphatic can include both substituted alkyl, alkenyl, and alkynyl and unsubstituted alkyl, alkenyl, and alkynyl.

As used herein, an "alkyl" group refers to a saturated aliphatic hydrocarbon group containing 1-10 (e.g., 1-6, 1-4, or 1, 2, 3, 4, 5, 6, 7, 8, 9, or 10) carbon atoms. As used herein, the terminology $C_{1-n}$ alkyl refers to an alkyl group containing 1-n carbon atoms. For example, $C_{1-5}$ alkyl refers to an alkyl group containing 1, 2, 3, 4, or 5 carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl.

As used herein, an "alkenyl" group refers to an aliphatic carbon group that contains 2-10 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl.

As used herein, an "alkynyl" group refers to an aliphatic carbon group that contains 2-10 (e.g., 2-6 or 2-4) carbon atoms and at least one triple bond. Like an alkyl group, an alkynyl group can be straight or branched.

As used herein, an "aryl" group used alone or as part of a larger moiety as in "aralkyl", "aralkoxy", or "aryloxyalkyl", refers to an aromatic monocyclic ring ((e.g., phenyl) or an aromatic $C_8$-$C_{10}$ bicyclic (e.g., indenyl, naphthalenyl, tetrahydronaphthyl, tetrahydroindenyl).

As used herein, an "aralkyl" group refers to an alkyl group (e.g., a $C_{1-4}$ alkyl group) that is substituted with an aryl group. Both "alkyl" and "aryl" are defined herein. An example of an aralkyl group is benzyl.

A "heteroaralkyl" group refers to an alkyl group that is substituted with a heteroaryl. Both "alkyl" and "heteroaryl" are defined herein.

The term "cycloaliphatic" means a saturated or partially unsaturated monocyclic or bicyclic, hydrocarbon ring that has a single point of attachment to the rest of the molecule. Cycloaliphatic rings are 3-8 membered monocyclic rings (e.g., 3-6 membered rings). Cycloaliphatic rings also include 8-12 membered bicyclic hydrocarbon rings, (e.g., 10 membered bicyclic hydrocarbon rings). A cycloaliphatic group encompasses a "cycloalkyl" group and a "cycloalkenyl" group.

As used herein, a "cycloalkyl" group refers to a saturated carbocyclic mono-, bi-, tri-, or multicyclic (fused or bridged) ring of 3-10 (e.g., 4-6, 5-10, 3, 4, 5, 6, 7, 8, 9, or 10) carbon atoms. Without limitation, examples of monocyclic cycloalkyl groups include cyclopropyl, cyclobutyl, cyclopentyl, cyclohexyl, cycloheptyl, or the like.

As used herein spiroalkyl group is an alkyl group where the alkyl group is in a ring of 2-10 carbons, for example 2-5 carbons, or 1-3 carbons.

The terms "heterocycle" or "heterocyclic," or "heterocyclyl" as used herein indicates a fully saturated, partially saturated, or unsaturated 3- to 12-membered monocyclic or bicyclic ring having from 1 to 5 ring heteroatoms selected from O, S or N. The bicyclic heterocycles may be fused or spirocyclic ring systems.

As used herein, a "heterocycloalkyl" group refers to a 3-10 membered mono or bicyclic (fused or bridged) (e.g., 4-6, 5-10, 3, 4, 5, 6, 7, 8, 9, or 10-membered mono or bicyclic) saturated ring structure, in which one or more of the ring atoms is a heteroatom (e.g., N, O, S, or combinations thereof).

A "heteroaryl" group, as used herein, refers to a monocyclic, bicyclic, or tricyclic ring structure having 4 to 15 (e.g., 5-9, 6-13, 4, 5, 6, 7, 8, 9, 10, 11, 12, 13, 14, or 15) ring atoms wherein one or more of the ring atoms is a heteroatom (e.g., N, O, S, or combinations thereof), and wherein one or more rings of the bicyclic or tricyclic ring structure is aromatic.

Without limitation, monocyclic heteroaryls include furyl, thiophenyl, 2H-pyrrolyl, pyrrolyl, oxazolyl, thiazolyl, imidazolyl, pyrazolyl, isoxazolyl, isothiazolyl, 1,3,4-thiadiazolyl, 2H-pyranyl, 4-H-pyranyl, pyridyl, pyridazyl, pyrimidyl, pyrazolyl, pyrazyl, or 1,3,5-triazyl.

A "heteroaralkyl" group, as used herein, refers to an alkyl group (e.g., a $C_{1-4}$ alkyl group) that is substituted with a heteroaryl group. Both "alkyl" and "heteroaryl" have been defined above.

As used herein, a "carboxy" (or "carboxyl") and a "sulfo" group refer to —COOH or —COOR$^X$ and —SO$_3$H or —SO$_3$R$^X$, respectively.

As used herein, a "hydroxy" or "hydroxyl" group refers to —OH.

As used herein, an "alkoxy" or "alkoxyl" group refers to an alkyl-O— group where "alkyl" has been defined previously. Moreover an alkoxy group includes structures comprising two alkoxy groups on the same atom or adjacent atoms that form a ring together with the atom(s) to which they are bound.

As used herein, an "oxo" refers to =O.

Unless otherwise stated, structures depicted herein are also meant to include all isomers arising from chiral centers (e.g., enantiomeric, diastereisomeric) forms of the structure. Therefore, single stereochemical isomers as well as enantiomeric and diastereisomeric mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

DETAILED DESCRIPTION OF THE INVENTION

Experiments conducted during the course of the present invention indicate that dimethyl-nonatetraenyl-trimethyl-cyclohexyl compounds described herein have similar activity to ATRA in assays that predict anti-acne efficacy (keratinocyte detachment assay and epidermal thickening assay) and in assays that predict skin-repair efficacy (increased fibroblast survival and epidermal thickening). At the same time, the lack of cytokine generation with such compounds indicate that such compounds will, unlike ATRA, not cause the skin irritation response that is the classic result of topical ATRA use.

Accordingly, the present invention contemplates that exposure of animals (e.g., humans) suffering from disorders characterized by abnormal proliferation and/or abnormal differentiation of cells (e.g., cells of which the growth and differentiation is sensitive to the actions of retinoids) to therapeutically effective amounts of drug(s) having a dimethyl-nonatetraenyl-trimethyl-cyclohexyl structure (that mimic the activity of ATRA without related skin irritation) will produce efficacious responses similar to those of ATRA but without it's side effects.

The present invention contemplates that the dimethyl-nonatetraenyl-trimethyl-cyclohexyl compounds of the present invention satisfy an unmet need for the treatment of disorders situated in the field of oncology, for example, APL, neuroblastoma, head- and neck cancer, lung cancer, breast cancer, uterine cervix cancer, gastrointestinal tract cancer, skin cancer, bladder cancer and prostate cancer and similar disorders; and in the field of dermatology, for example, inflammatory/keratinization disorders such as rosacea, acne, psoriasis, severe psoriasis, lamellar ichthyosis, plantar warts, callosities, acanthosis *nigricans*, lichen planus, molluscum, melasma, corneal epithelial abrasion, geographic tongue, Fox-Fordyce disease, cutaneous metastatic melanoma and keloids, epidermolytic hyperkeratosis, Darier's disease, *pityriasis rubra* pilaris, congenital ichthyosiform erythroderma, hyperkeratosis palmaris et plantaris, melasma, hyperpigmentation and similar disorders.

The present invention contemplates that the dimethyl-nonatetraenyl-trimethyl-cyclohexyl compounds of the present invention satisfy an unmet need for the treatment of such disorders either when administered as monotherapy, or when administered in a temporal relationship with additional agent(s), such as other pharmaceutical agents known to be useful in treating such disorders (combination therapies).

Indeed, the Applicants have found that certain dimethyl-nonatetraenyl-trimethyl-cyclohexyl compounds serve as therapeutics for the treatment of disorders in the field of oncology, for example, APL, neuroblastoma, head- and neck cancer, lung cancer, breast cancer, uterine cervix cancer, gastrointestinal tract cancer, skin cancer, bladder cancer and prostate cancer and similar disorders; and in the field of dermatology, for example, keratinization disorders such as rosacea, acne, psoriasis, severe psoriasis, lamellar ichthyosis, plantar warts, callosities, acanthosis *nigricans*, lichen planus, molluscum, melasma, corneal epithelial abrasion, geographic tongue, Fox-Fordyce disease, cutaneous metastatic melanoma and keloids, epidermolytic hyperkeratosis, Darier's disease, *pityriasis rubra* pilaris, congenital ichthyosiform erythroderma, hyperkeratosis palmaris et plantaris, melasma, hyperpigmentation and similar disorders. Certain dimethyl-nonatetraenyl-trimethyl-cyclohexyl compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

As such, the present invention provides a new class of small-molecules having a dimethyl-nonatetraenyl-trimethyl-cyclohexyl structure useful as therapeutics for the treatment of skin conditions within the fields of, for example, oncology and dermatology.

In a particular embodiment, dimethyl-nonatetraenyl-trimethyl-cyclohexyl compounds encompassed within Formula I are provided:

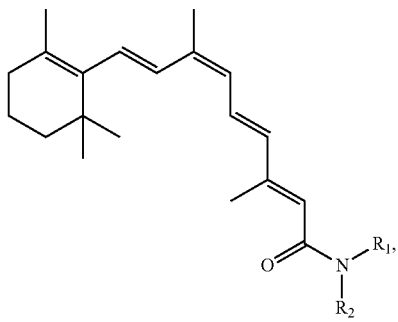

including pharmaceutically acceptable salts, solvates, and/or prodrugs thereof.

In some embodiments, $R_1$ is $CH_3$, $CF_3$, or an optionally substituted saturated or unsaturated alkyl chain moiety having two or more carbon molecules.

In some embodiments, $R_1$ is $CH_3$, $CF_3$, or $C_{2-4}$ alkyl.

In some embodiments, $R_1$ is $CH_3$, $CF_3$, or is a straight or branched carbon chain of 1-10 carbon atoms, which can contain up to two double or triple bonds, as allowed by valency, and can be optionally substituted with up to three substituents.

In some embodiments wherein the $R_1$ moiety is optionally substituted, such a $R_1$ moiety is optionally substituted with a saturated or unsaturated alkyl chain, a saturated or unsaturated cycloalkyl moiety, a saturated or unsaturated branched-alkyl moiety, a halogen (e.g., chlorine, fluorine, bromine, iodine), an optionally substituted cyano-moiety, an optionally substituted oxo-moiety (e.g., =O), or

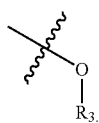

In some embodiments, $R_2$ is

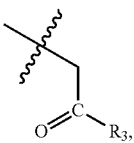

$CH_3$, $CF_3$, or an optionally substituted saturated or unsaturated alkyl chain moiety having two or more carbon molecules.

In some embodiments, $R_2$ is $CH_3$, $CF_3$, or is a straight or branched carbon chain of 1-10 carbon atoms, which can contain up to two double or triple bonds, as allowed by valency, which can be optionally substituted with up to three substituents.

In some embodiments wherein the $R_2$ moiety is optionally substituted, such a $R_2$ moiety is optionally substituted with a saturated or unsaturated alkyl chain, a saturated or unsaturated cycloalkyl moiety, a saturated or unsaturated branched-alkyl moiety, a halogen e.g., chlorine, fluorine, bromine, iodine), an optionally substituted cyano-moiety, an optionally substituted oxo-moiety (e.g., =O), $CH_2(CO)R_3$, or

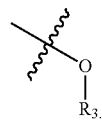

In some embodiments, R1 and R2 are different.

In some embodiments,

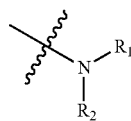

form an optionally substituted cyclic moiety having from 4-7 carbon atoms, optionally substituted with up to three groups chosen independently $C_{1-10}$ alkyl, $C_{3-10}$ alkenyl, $C_{3-10}$ alkynyl, all of which may be straight chain or branched $C_{3-10}$ cycloalkyl, $C_{2-5}$ spiroalkyl, halogen, cyano, oxo, $CF_3$ or $OR_3$, such that when $R_3$ is bonded directly to oxygen, it is $R_4$.

In some embodiments, such an

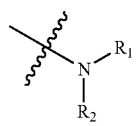

moiety formed as an optionally substituted cyclic moiety having from 4-7 carbon atoms is selected from

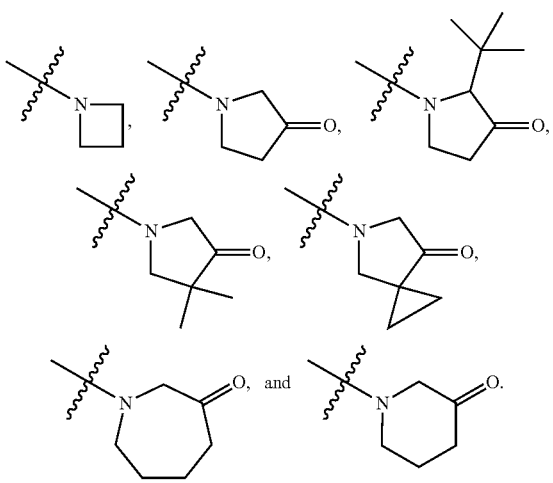

In some embodiments, $R_3$ is an optionally substituted saturated or unsaturated alkyl chain moiety having two or more carbon molecules.

In some embodiments, R3 is

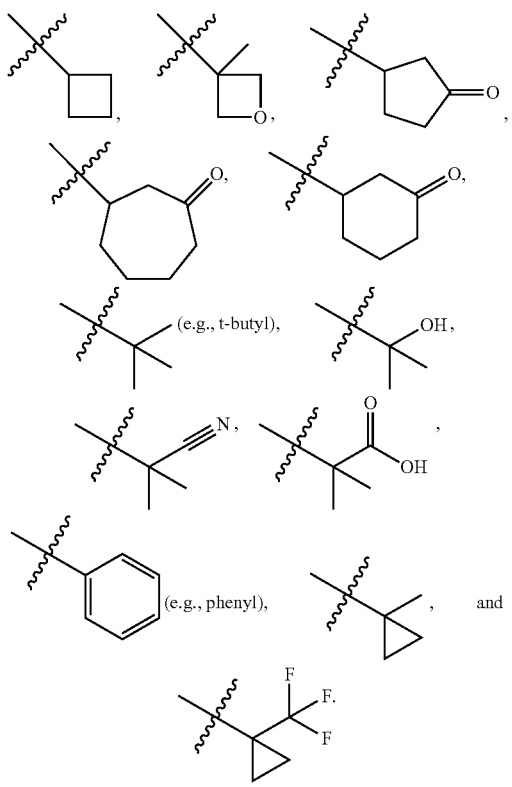

In some embodiments $R_1$ and $R_2$, along with the nitrogen both are bonded to can form a ring having 4-7 atoms, optionally substituted with up to three groups chosen independently $C_{1-10}$ alkyl, $C_{3-10}$ alkenyl, $C_{3-10}$ alkynyl, all of which may be straight chain or branched $C_{3-10}$ cycloalkyl, $C_{2-5}$ spiroalkyl, halogen, cyano, oxo, $CF_3$ or $OR_3$, such that when $R_3$ is bonded directly to oxygen, it is $R_4$.

In some embodiments, $R_3$ is $C_{2-10}$ alkyl, $C_{2-10}$ alkenyl, $C_{2-10}$ alkynyl, all of which may be straight chain or branched, phenyl, monocyclic or bicyclic 5-10 membered heteroaryl containing up to four heteroatoms chosen from N, O and S, $C_{3-7}$ cycloalkyl, 4-7 membered heterocycloalkyl, optionally substituted with up to three groups chosen independently from $C_{1-10}$ alkyl, $C_{3-10}$ cycloalkyl, $C_{2-10}$ alkenyl $C_{3-10}$ cycloalkenyl, $C_{2-10}$ alkynyl, $C_{3-10}$ branched alkyl, $C_{3-10}$ branched alkenyl, $C_{4-10}$ branched alkynyl, $C_{2-5}$ spiroalkyl, halogen, hydroxy, carboxy, cyano, oxo, or $CF_3$.

In some embodiments, $R_4$ is $C_{1-4}$ lower alkyl straight chain or branched, $C_{3-4}$, alkenyl straight chain or branched, $C_{3-4}$ alkynyl, $C_{2-4}$ lower acyl, $CF_3$ or $C_2$ fluoroalkyl.

In some embodiments, $R_4$ is $C_{1-4}$ alkyl.

In certain embodiments, the compounds of Formula 1 described immediately above can have $R_1$ or $R_2$ or $R_3$ each with up to three substituents are independently chosen from, $C_{3-8}$ cycloalkyl, $C_{4-8}$ cycloalkenyl, halo, CN, $N_3$, $CF_3$, $NO_2$, cycloalkyl, substituted cycloalkyl, cycloalkenyl substituted cycloalkenyl, heterocycloalkyl, phenyl, substituted phenyl, heteroaryl, substituted heteroaryl, hydroxy, oxo, thio, thiono, amino, cyano, $C_{1-6}$ alkoxy, $C_{3-6}$ cycloalkoxy, $C_{1-6}$ alkylthio, $C_{3-6}$ cycloalkylthio, $C_{1-6}$ alkylsulfonyl, $C_{3-6}$ cycloalkylsylfonyl, monoalkylamino, dialkylamino, monocycloalkylamino, or bis(cycloalkyl)amino.

In some embodiments of the compounds of Formula I described immediately above $R_1$ is $CH_3$, $CF_3$, $C_{2-10}$ alkyl, $C_{3-10}$ alkenyl, $C_{3-10}$ alkynyl, all of which may be straight chain or branched, or $CF_3$, which can be optionally substituted with up to three groups chosen independently from $C_{1-10}$ alkyl, $C_{3-10}$ cycloalkyl, $C_{2-10}$ alkenyl $C_{3-10}$ cycloalkenyl, $C_{2-10}$ alkynyl, wherein all aliphatics may be straight chain or branched, halogen, hydroxy, cyano, oxo, $CF_3$ or $OR_3$, such that when $R_3$ is bonded directly to oxygen, it is $R_4$; and independently $R_2$ is $C_{1-10}$ alkyl, $C_{3-10}$ alkenyl, $C_{3-10}$ alkynyl, all of which may be straight chain or branched, or $CF_3$, which can be optionally substituted with up to three groups chosen independently from $C_{1-10}$ alkyl, $C_{3-10}$ cycloalkyl, $C_{2-10}$ alkenyl $C_{3-10}$ cycloalkenyl, $C_{2-10}$ alkynyl, wherein all aliphatics may be straight chain or branched, halogen, hydroxy, cyano, oxo, $CF_3$ or $OR_3$, such that when $R_3$ is bonded directly to oxygen, it is $R_4$.

In some embodiments, the following compounds are contemplated for Formula I:

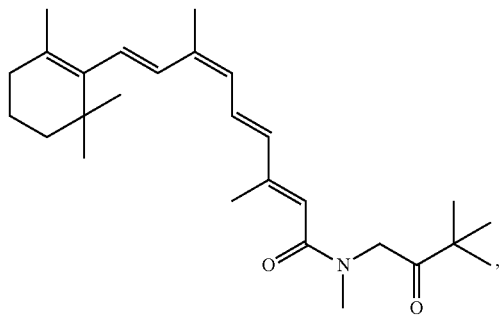

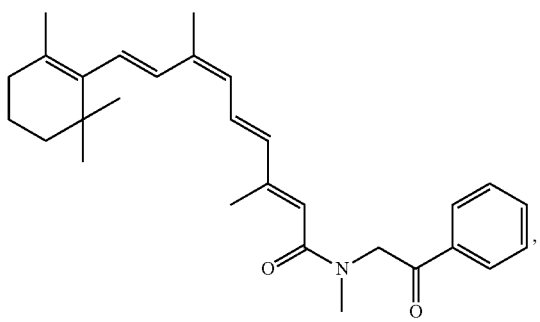

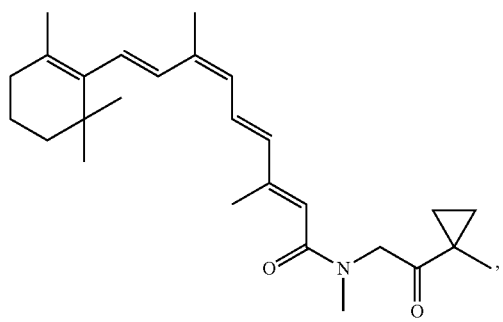

-continued
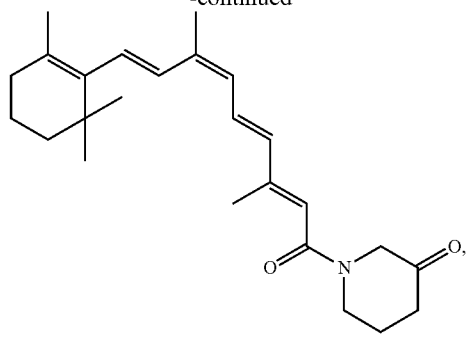
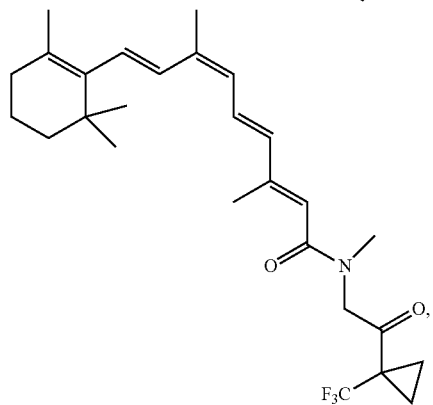
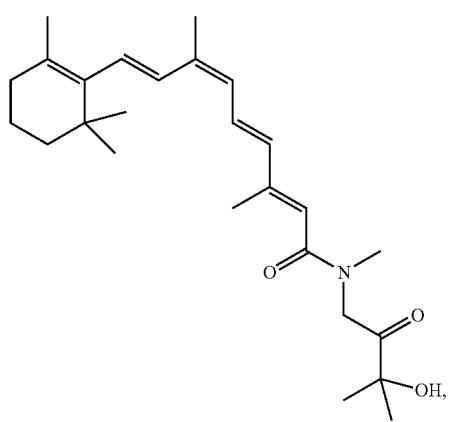
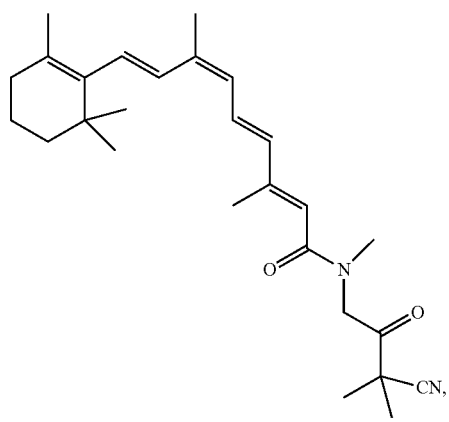
-continued
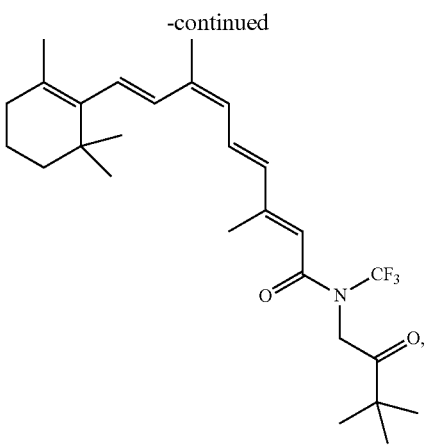
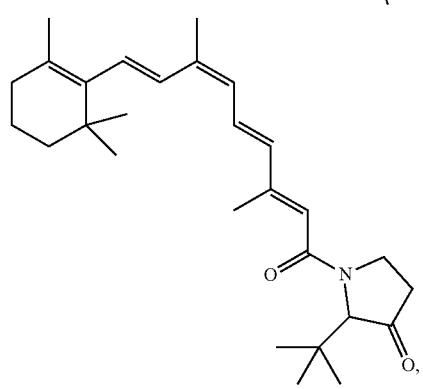
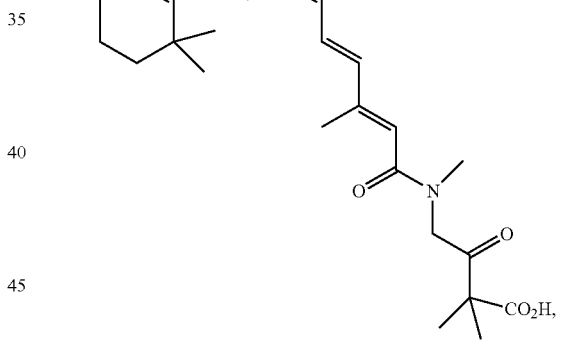
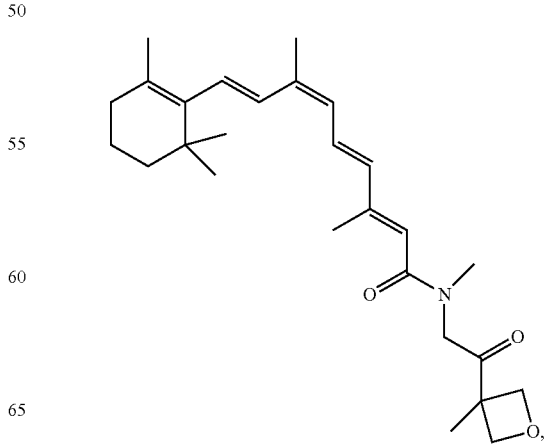

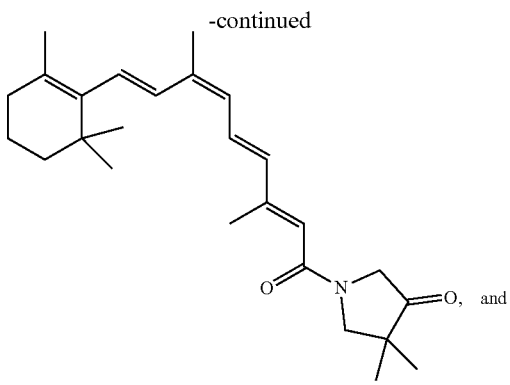

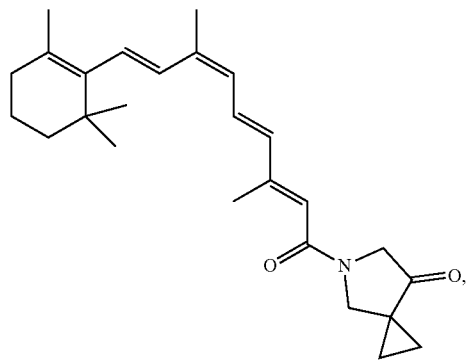

or a pharmaceutically acceptable salt, solvate, or prodrug thereof.

The invention also provides pharmaceutical compositions comprising the compounds of the invention in a pharmaceutically acceptable carrier.

Thus, the present invention also relates to the compounds described herein for use as a medicine, in particular, for use in the manufacture of a medicament for the treatment of oncology disorders and keratinization disorders.

In certain embodiments of the invention, combination treatment of animals with a therapeutically effective amount of a compound of the present invention and a course of an additional pharmaceutical agent useful in treating such oncological and/or dermatological disorders produces a greater response and clinical benefit in such animals compared to those treated with the compound or additional agent alone. Since the doses for all approved drugs are known, the present invention contemplates the various combinations of them with the present compounds.

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN—α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-κB modulators; anti-CDK compounds; HDAC inhibitors; and the like. Numerous other examples of chemotherapeutic compounds and anticancer therapies suitable for co-administration with the disclosed compounds are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); antiandrogens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide a compound of the invention and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N—methylhydrazine; MIH)); 10) adrenocortical suppressants (e.g., mitotane (o,p'—DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 3 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4 H-pyrazolo[3,4-d]pyrimidin-4-one monosodium salt) | Zyloprim | GlaxoSmithKline, Research Triangle Park, NC |
| Altretamine (N,N,N',N',N'',N''-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus* Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-, (SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |

TABLE 1-continued

| | | |
|---|---|---|
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |

TABLE 1-continued

| | | |
|---|---|---|
| Goserelin acetate | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperidinopiperidino)carbonyloxy]-1H-pyrano[3',4':6,7] indolizino[1,2-b] quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S \cdot HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6 H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β,20-Epoxy-1,2a,4,7β,10β,13a-hexahydroxytax-11-en-9-one 4,10-diacetate 2-benzoate 13-ester with (2R,3S)-N-benzoyl-3-phenylisoserine) | TAXOL | Bristol-Myers Squibb |

TABLE 1-continued

| | | |
|---|---|---|
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-µ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine,1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4': 6,7] indolizino [1,2-b] quinoline-3,14-4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |

TABLE 1-continued

| | | |
|---|---|---|
| Vinblastine, Leurocristine ($C_{46}H_{56}N_4O_{10}\cdot H_2SO_4$) | Velban | Eli Lilly |
| Vincristine ($C_{46}H_{56}N_4O_{10}\cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN—161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-15992, SGN—0010, SGN—40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN—1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods for administering a compound of the invention with radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tirapazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the present invention, a compound of the invention and one or more therapeutic agents or anticancer agents are administered to an animal under one or more of the following conditions: at different periodicities, at different durations, at different concentrations, by different administration routes, etc. In some embodiments, the compound is administered prior to the therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic or anticancer agent. In some embodiments, the compound is administered after the therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

For ease of administration, the subject compounds may be formulated into various pharmaceutical forms. As appropriate compositions there may be cited all compositions usually employed for systemically or topically administering drugs. To prepare the pharmaceutical compositions of this invention, a retinoic mimetic effective amount of the particular compound, optionally in addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g. as a transdermal patch, as a spot-on or as an ointment. Addition salts of compounds of formula (I) due to their increased water solubility over the corresponding base form, are obviously more suitable in the preparation of aqueous compositions.

As appropriate compositions for topical application there may be cited all compositions usually employed for topically administering drugs e.g. creams, gellies, dressings, shampoos, tinctures, pastes, ointments, salves, powders and the like. Application of said compositions may be by aerosol, e.g. with a propellant such as nitrogen, carbon dioxide, a Freon, or without a propellant such as a pump spray, drops, lotions, or a semisolid such as a thickened composition which can be applied by a swab. In particular compositions, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (included scored or coated tablets), capsules, pills, powder packets, wafers, injectable solutions or suspensions, teaspoonfuls, tablespoonfuls and the like, and segregated multiples thereof.

Other such compositions are preparations of the cosmetic type, such as toilet waters, packs, lotions, skin milks or milky lotions. Said preparations contain, besides the active ingredient, components usually employed in such preparations. Examples of such components are oils, fats, waxes, surfactants, humectants, thickening agents, antioxidants, viscosity stabilizers, chelating agents, buffers, preservatives, perfumes, dyestuffs, lower alkanols, and the like. If desired, further ingredients may be incorporated in the compositions, e.g. antiinflammatory agents, antibacterials, antifungals, disinfectants, vitamins, sunscreens, antibiotics, or other anti-acne agents.

The present invention also provides particular pharmaceutical or cosmetical compositions which comprise a pharmaceutically acceptable carrier, an effective amount of a compound of formula (I) and an effective amount of a retinoic acid, a derivative thereof or a stereochemically isomeric form thereof. Said retinoic acid containing compositions are particularly useful for treating acne or for retarding the effects of aging of the skin and generally improve the quality of the skin, particularly human facial skin.

Further, the invention also relates to particular pharmaceutical or cosmetical compositions which comprise a pharmaceutically acceptable carrier, an effective amount of a compound of formula (I) and an effective amount of calcitriol or a prodrug thereof. The latter compositions are particularly useful in treating keratinization disorders.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient which may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example 1

Synthesis of (2E,4E 6Z,8E)-N-(3,3-dimethyl-2-oxobutyl)-N,3,7-trimethyl-9-(2,6,6-trimethylcyclohex-1-en-1-yl)nona-2,4,6,8-tetraenamide (1)

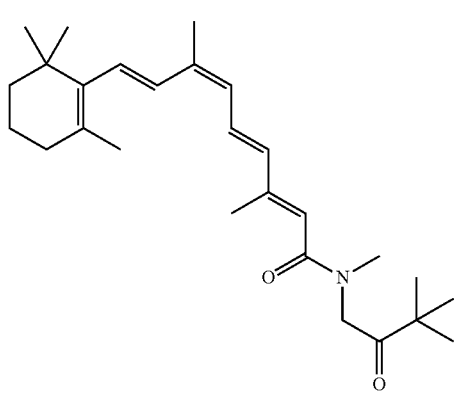

1

3,3-Dimethyl-1-(methylamino)butan-2-one

1-Bromopinacolone (1 g, 5.58 mmol) was taken up in 10 mL acetonitrile followed by the addition of triethylamine (0.56 g, 5.56 mmol) and 40% aqueous methyl amine (0.48 g, 6.2 mmol). The solution was stirred at room temperature for overnight and then concentrated in vacuo. The resulting residue was triturated with diethylether and the solid was collected by filtration. The solid was suspended in 25 mL ethyl acetate and treated dropwise with 1M NaOH (7 ml). The organic phase was separated, dried ($Na_2SO_4$), and concentrated to give 3,3-dimethyl-1-(methylamino)butan-2-one (0.33 g, 46%) as a yellow oil. CI-MS $[M+H]^+$130.08

(2E,4E 6Z,8E)-N-(3,3-dimethyl-2-oxobutyl)-N—3,7-trimethyl-9-(2,6,6-trimethylcyclohex-1-en-1-yl)nona-2,4,6,8-tetraenamide (1)

9-cis-Retinoic acid (0.25 g, 0.83 mmol) was suspended in 10 mL of dichloromethane and cooled to 0° C. To the mixture was added triethylamine (0.084 g, 0.83 mmol), 3,3-dimethyl-1-(methylamino)butan-2-one (0.33 g, 2.5 mmol), and 1-ethyl-3-(3-dimethylaminopropyl)carbodiimide (EDC; 0.20 g, 1 mmol) respectively. The solution gradually warmed to room temperature and was stirred in the dark for overnight. The solution was washed with water, dried ($Na_2SO_4$), and concentrated to a brown oil. The crude product was taken up in 4:1 hexane/ethyl acetate and purified using silica gel chromatography (elution with 4:1 hexane/ethyl acetate). Fractions containing the product were combined and concentrated to yield 1 (0.20 g, 59%) as a yellow viscous liquid. CI-MS $[M+H]^+$412.33; $^1$HNMR ($CDCl_3$) δ 6.92 (dd, 1H), 6.62 (d, 1H), 6.24 (m, 2H), 6.04 (d, 1H), 6.01 (s, 1H), 4.4 (s, 2H), 3.01 (s, 3H), 2.14 (s, 3H), 2.04 (m, 2H), 1.97 (s, 3H), 1.74 (s, 3H), 1.64 (m, 2H), 1.49 (m, 2H), 1.22 (s, 9H), 1.03 (s, 6H) ppm.

Example 2

Synthesis of (2E,4E 6Z,8E)-N,3,7-trimethyl—N-(2-oxo-2-phenylethyl)-9-(2,6,6-trimethylcyclohex-1-en-1-yl)nona-2,4,6,8-tetraenamide (2)

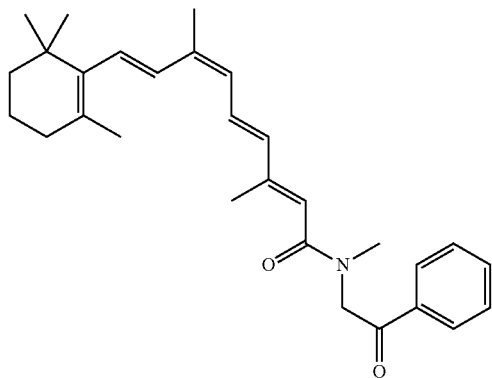

2

2-(Methylamino)-1-phenylethanone

2'-Bromoacetophenone (0.50 g, 2.5 mmoles) was taken up in diethyl ether (25 mL) and treated with 40% aq. methylamine (0.195 g, 2.5 mmol) in one portion. The reaction mixture was stirred at room temperature for overnight at which time the solvent was decanted and the remaining solid was dried under high vacuum. The solid afforded 0.17 g (30%) of 2-(methylamino)-1-phenylethanone as the HBr salt. CI-MS [M+H]$^+$150.08

(2E,4E 6Z,8E)-N,3,7-trimethyl—N-(2-oxo-2-phenylethyl)-9-(2,6,6-trimethylcyclohex-1-en-1-yl)nona-2,4,6,8-tetraenamide (2)

9-cis-Retinoic acid (0.25 g, 0.66 mmol) was suspended in 10 mL of dichloromethane and cooled to 0° C. To the mixture was added triethylamine (0.074 g, 0.73 mmol), 2-(methylamino)-1-phenylethanone (0.17 g, 0.73 mmol), and EDC (0.13 g, 0.68 mmol) respectively. The solution gradually warmed to room temperature and was stirred in the dark for overnight. The solution was washed with water, dried (Na$_2$SO$_4$), and concentrated to a brown oil. The crude product was taken up in 4:1 hexane/ethyl acetate and purified using silica gel chromatography (elution with 4:1 hexane/ethyl acetate). Fractions containing the product were combined and concentrated to yield 2 (0.060 g, 21%) as a yellow viscous liquid. CI-MS [M+H]$^+$432.31; $^1$HNMR (CDCl$_3$) δ 7.97 (d, 2H), 7.73 (m, 1H), 7.52 (m, 2H), 6.92 (dd, 1H), 6.62 (d, 1H), 6.24 (m, 2H), 6.07 (s, 1H), 6.03 (d, 1H), 4.89 (s, 2H), 3.12 (s, 3H), 2.17 (s, 3H), 2.04 (m, 2H), 1.97 (s, 3H), 1.74 (s, 3H), 1.64 (m, 2H), 1.49 (m, 2H), 1.03 (s, 6H) ppm.

Example 3

Synthesis of 1-((2E,4E 6Z,8E)-3,7-dimethyl-9-(2,6,6-trimethylcyclohex-1-en-1-yl)nona-2,4,6,8-tetranonyl)piperidin-3-one (4)

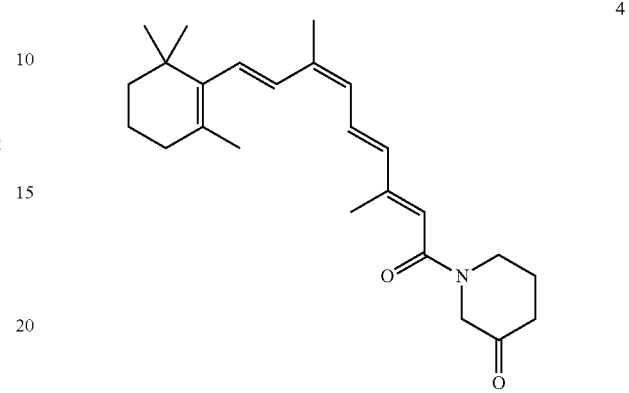

4

1N-((2E,4E 6Z,8E)-3,7-dimethyl-9-(2,6,6-trimethylcyclohex-1-en-1-yl)nona-2,4,6,8-tetranonyl)piperidin-3-one (4)

9-cis-Retinoic acid (0.10 g, 0.33 mmol) and piperid-3-one hydrochloride (0.054 g, 0.4 mmol) were suspended in 5 mL of dichloromethane and cooled to 0° C. To the mixture were added triethylamine (0.08 g, 0.8 mmol) and EDC (0.077 g, 0.4 mmol). The solution gradually warmed to room temperature and was stirred in the dark for overnight. The solution was washed with water, dried (Na$_2$SO$_4$), and concentrated to a brown oil. The crude product was taken up in dichloromethane and purified utilizing silica gel chromatography (elution with 1:1 hexane/ethyl acetate) to afford compound 3 (0.029 g, 24%) as a viscous yellow liquid. CI-MS [M+H]$^+$382.15; $^1$HNMR (CDCl$_3$) δ 6.94 (m, 1H), 6.62 (d, 1H), 6.24 (m, 2H), 6.03-5.86 (m, 2H), 4.24 (d, 2H), 3.81 (d, 2H), 2.54 (t, 2H), 2.12-2.02 (m, 4H), 1.98 (s, 3H), 1.74 (s, 3H), 1.66 (m, 2H), 1.56 (s, 3H), 1.48 (m, 2H), 1.04 (s, 6H) ppm.

Example 4

Synthesis of (2E,4E,6Z,8E)-N,3,7-trimethyl—N-(2-(1-methylcyclopropyl)-2-oxoethyl)-9-(2,6,6-trimethylcyclohex-1-en-1-yl)nona-2,4,6,8-tetraenamide (3)

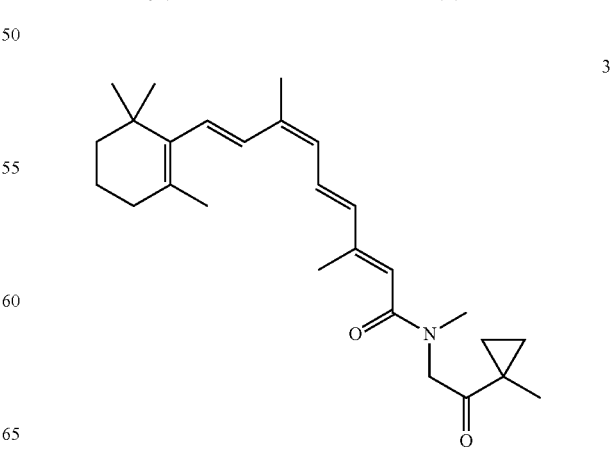

3

2-(Methylamino)-1-(1-methylcyclopropyl)ethanone 1-(1-Methylcyclopropyl)ethanone (1 g, 10 mmol) was taken up in methanol (50 mL) and cooled in an ice bath to 0° C. To the cold solution was added 1.8 g of bromine. The solution gradually warmed to room temperature and was stirred for overnight. The solvent was concentrated in vacuo and the crude product was purified using silica gel chromatography (elution with 3% ethyl acetate/hexane) to afford 2-bromo-1-(1-methylcyclopropyl)ethanone 0.94 g (53%) as a colorless liquid. The bromoketone (0.5 g, 2.8 mmol) was taken up in 5 mL of acetonitrile followed by the addition of triethylamine (0.28 g, 2.8 mmol) and 40% aqueous methylamine (0.24 g, 3.1 mmol). The solution was stirred at room temperature for 3 hours and then concentrated in vacuo. The resulting solid was triturated with diethyl ether and the solvent was removed by filtration. The crude solid was dried under high vacuum for overnight. The solid was suspended in 25 mL of diethyl ether and washed with 5 mL of 1M NaOH. The organic phase was separated, dried ($Na_2SO_4$), and concentrated to give 2-(methylamino)-1-(1-methylcyclopropyl)ethanone (0.25 g, 71%) as a brown oil. CI-MS [M+H]$^+$ 128.07

(2E,4E,6Z,8E)-N,3,7-trimethyl—N-(2-(1-methylcyclopropyl)-2-oxoethyl)-9-(2,6,6-trimethylcyclohex-1-en-1-yl)nona-2,4,6,8-tetraenamide (3)

9-cis-Retinoic acid (0.23 g, 0.76 mmol) was suspended in 10 mL of dichloromethane and cooled to 0° C. To the mixture was added triethylamine (0.15 g, 0.1.5 mmol), 2-(methylamino)-1-(1-methylcyclopropyl)ethanone (0.20 g, 1.5 mmol), and EDC (0.17 g, 0.89 mmol) respectively. The solution gradually warmed to room temperature and was stirred in the dark for overnight. The solution was washed with water, dried ($Na_2SO_4$), and concentrated to a brown oil. The crude product was taken up in 4:1 hexane/ethyl acetate and purified using silica gel chromatography (elution with 4:1 hexane/ethyl acetate). Fractions containing the product were combined and concentrated to yield 4 (0.069 g, 22%) as a yellow viscous liquid. CI-MS [M+H]$^+$410.25; $^1$HNMR (CDCl$_3$) δ 6.92 (dd, 1H), 6.62 (d, 1H), 6.24 (m, 2H), 6.03 (d, 1H), 6.01 (s, 1H), 4.35 (s, 2H), 3.02 (s, 3H), 2.14 (s, 3H), 2.04 (m, 2H), 1.97 (s, 3H), 1.74 (s, 3H), 1.64 (m, 2H), 1.49 (m, 2H), 1.38 (s, 3H), 1.33 (m, 2H), 1.03 (s, 6H), 0.76 (m, 2H) ppm.

Example 5. In Vitro Assays

A. Repair of Skin Damage

This example demonstrates that the compounds of the present invention have similar activity to ATRA in assays that predict anti-acne efficacy (keratinocyte detachment assay and epidermal thickening assay) and in assays that predict skin-repair efficacy (increased fibroblast survival and epidermal thickening.

Fibroblast Culture Protocol.

Human dermal fibroblasts are isolated from skin biopsies as described previously and grown in monolayer culture using DMEM supplemented with 10% fetal bovine serum as culture medium (see, e.g., Varani J, et al., J Clin Invest. 1994; 94; Varani J, et al., *J. Invest. Dermatol.* 94:717-723, 1990). Growth is at 37° C. in a humidified atmosphere containing 5% $CO_2$ and 95% air. For experimental studies, cells are plated at 5×10$^4$ cells per well in wells of a 24-well culture dish in the same culture medium. One day later, cells are washed and the DMEM culture medium is replaced with Keratinocyte Basal Medium (KBM).

Keratinocyte Culture Protocol.

Human epidermal keratinocytes are isolated from the same skin biopsies as fibroblasts and grown in monolayer culture using Keratinocyte Growth Medium (KGM) as described previously (see, e.g., Varani J, et al., J Clin Invest. 1994; Varani J, et al., *J. Invest. Dermatol.* 94:717-723, 1990; Varani J, et al., J. Invest. Dermatol. 1989; 93:449-454). Growth is at 37° C. in a humidified atmosphere containing 5% $CO_2$ and 95% air. For some studies, experiments use the HaCat line of immortalized human epidermal keratinocytes in place of primary or low-passage cells. Growth for these cells is exactly as with low-passage keratinocytes.

Human Skin Organ Culture Protocol.

Replicate 2-mm punch biopsies (up to 12 per subject) are obtained from hip skin of volunteers 18-70 years of age. The participation of human subjects is approved by the University of Michigan Institutional Review Board and all subjects provide written informed consent prior to their inclusion in the study. The punch biopsies are incubated in wells of a 24 well dish (one tissue piece per 200-500 μL of culture medium). Culture medium consists of KBM. For organ culture, the culture medium is supplemented with calcium chloride to a final calcium concentration of 1.5 mM. One or two wells are typically left as control while the others are treated as desired. Fresh culture medium and treatments are provided at 2-day intervals. Organ culture-conditioned medium collected at day-2 is saved for cytokine assessment or for measure of other bioactive molecules as desired. At the end of the incubation period (typically, day-8), the tissue is fixed in 10% buffered formalin and used for histology. The organ culture protocol used here is virtually identical to that described in several past reports (see, e.g., Varani J, et al., J Clin Invest. 1994; 94:1747-1756; Varani J, et al., Am J Pathol. 1993 January; 142(1):189-98; Lateef H, et al., Am J Pathol. 2004; 165:167-174; Varani J, et al., Exp Mol Pathol. 2004; 77(3):176-83; Varani J, et al., Am J Pathol. 1993 June; 142(6):1813-22; Varani J, et al., *Toxicol. Pathol.* 35:693-701, 2007; Rittié L, et al., *J Invest Dermatol,* 126:732-739, 2006).

Retinoid-Induced Fibroblast Survival.

In this assay, low-passage human dermal fibroblasts are grown for three days in Keratinocyte Basal Medium (KBM) at a calcium concentration (0.1 mM) that is too low to support survival. Over the three day period, a majority of the cells die. Biologically active retinoids including all-trans retinoic acid (ATRA) are known to protect cells from cell lysis in this assay (see, e.g., Varani J, et al., *J. Invest. Dermatol.* 94:717-723, 1990). How retinoids act to prevent fibroblast lysis is not fully understood, but part of the mechanism involves modulation of calcium transit across the cell membrane in the presence of the active retinoids (see, e.g., Varani J, et al., *Am. J. Path.* 136:1275-1281, 1990; Varani K, et al., *Am J. Pathol.* 147:718-729, 1995; Varani J, et al., *Amer. J. Pathol.* 148: 1307-1312, 1996).

For the studies depicted in FIG. 2, human dermal fibroblasts were treated with ATRA and with compounds 1-4 over a range of concentrations from 0.1 to 5 μg/mL. The values shown represent the percentage of the initially present cells that were still viable after the three day incubation period. It can be seen from the figure that with ATRA, protection was optimal at 1.0 μg/mL. Lower concentrations had less protection. The fall-off in cell numbers at 5 μg/mL represents incipient toxicity. As seen in the FIG. 5, Compound 1 was as effective as ATRA. The three other retinoids, Compounds 2-4, were also protective, although the effective concentration range was higher than that with ATRA and Compound 1.

Retinoid-Induced Fibroblast Cytotoxicity.

This assay is similar to the fibroblast cytotoxicity assay except that the human dermal fibroblasts are plated in culture medium (KBM) supplemented with a concentration of calcium (1.5 mM) that supports survival on its own. The biologically active retinoids are included in the culture medium and the cells incubated for 72 hours. Under such conditions, there is little net increase in growth with added retinoid, and at high concentrations, cytotoxicity occurs (see, e.g., Varani, J., et al., *J. Invest. Dermatol.* 101:839-842).

It can be seen from the data presented in FIG. 3 that the novel retinoids had a similar profile of cytotoxicity as ATRA. That is, there was little decline in cell numbers compared to control with retinoid concentrations up to 5 µg/mL.

Generation of Pro-Inflammatory Cytokines.

ATRA and other biologically-active retinoids are known to induce the production of pro-inflammatory cytokines in human skin (see, e.g., Varani J, et al., *Toxicol. Pathol.* 35:693-701, 2007; Perone P, et al., Arch Dermatol Res. 2007; 298:439-448) as well as in other cells/tissues (see, e.g., Aslam M N, et al., Anti-Cancer Drugs 2015, 26:763-773). Among the cytokines that are up-regulated in response to retinoid treatment are tumor necrosis factor-α (TNF-α), interleukin (IL) 1-β, IL-6, IL-8 and macrophage chemotactic peptide-1 (MCP-1). It is believed that the pro-inflammatory cytokines are "drivers" of the retinoid-induced skin irritation response. When released systemically, the same cytokines are likely to underlie much of the retinoid-induced toxicity seen, for example, when ATRA is used to treat acute myeloid leukemia (see, e.g., Frankel S R, et al., Ann Intern Med. 1992; 117:292-296; Vandat L, et al., *Blood.* 1994; 84(11): 3843-3849; De Botton S, et al., *Blood.* 1998; 92(8):2712-2718). In this experiment, fibroblasts were cultured for two days in KBM supplemented with 1.5 mM calcium (i.e., as in the cytotoxicity assay). Culture fluids were collected after two days of incubation and subjected to a multiplex enzyme-linked immunosorbant assay (ELISA) for the following cytokines: TNF-α, IL-1β, IL-6, IL-8, MCP-1 and CXCL-1. As seen in FIG. 4, ATRA induced a strong up-regulation of several cytokines while this was not observed with either Compound 1 or 2. In a second experiment, ATRA was compared to Compounds 3 and 4 in the same assay. Both retinoids generated much lower levels of the various cytokines than did ATRA. Compound 4 was comparable to Compound 1.

Retinoid-Induced Keratinocyte "Desquamation."

When keratinocytes are grown in monolayer culture, proliferation is optimal under low-calcium (0.05-0.15 mM) conditions. When the calcium concentration is raised to 1.5 mM, the keratinocyte differentiation occurs and proliferation slows. Under such conditions, strong cell-cell connections are made. Keratinocyte treatment with biologically-active retinoid such as ATRA reduces differentiation and leads to reduction in cell-cell connections. The end result is that cells separate more easily from one another (see, e.g., Varani J, et al., J. Invest. Dermatol. 1989; 93:449-454; Varani J, et al., *J Invest. Dermatol.* 97:917-921, 1991; Varani J, et al., *Am. Path.* 138:887-895, 1991). Retinoid efficacy in acne is dependent, in part at least, on reduced epidermal cohesion and ability of acne lesional skin to slough during washing.

Figure 5:
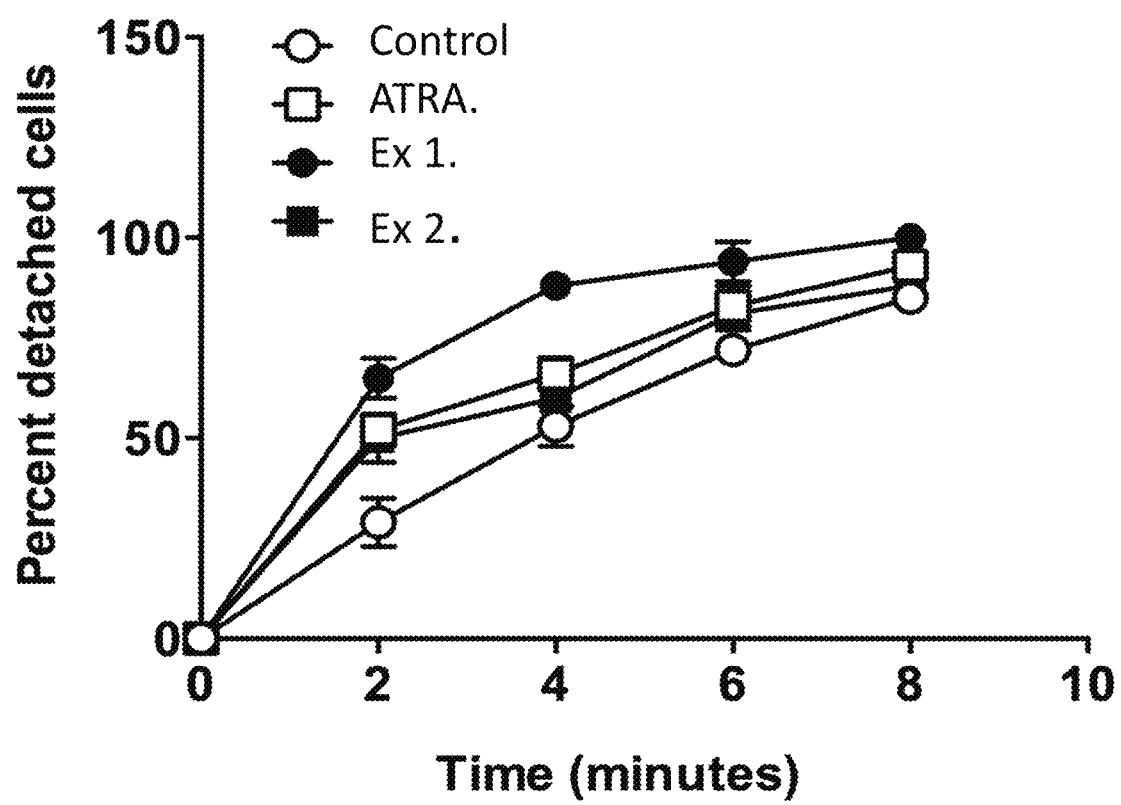
FIG. 5: Comparison Examples 1 & 2 with control and with ATRA for induction of cell-cell detachment in epidermal keratinocytes. Keratinocytes were grown for two days in KBM supplemented with 1.5 mM calcium (control) and treated with ATRA or Example 1 at 1.0 µg/mL or with Example 2 at 2.5 µg/mL. At the end of the incubation period, the cells were exposed to a combination of trypsin and EDTA and the percentage of cells that detached from one another were assessed over time. All three retinoids increased the ease of cell-cell separation as compared to control. At 1 µg/mL, Example 1 was more potent than ATRA. At 2.5 µg/mL, Example 2 was comparable to ATRA at 1 µg/mL. The values are means and standard deviations based on n=9 data points for ATRA and Example 1 and 6 data points for Example 2.

As a way to quantify detachment, keratinocytes grown for 2 days in culture medium containing 1.5 mM calcium were washed and exposed to a combination of trypsin and EDTA. Cell detachment from neighboring cells was assessed at timed intervals. The data presented in FIG. 5 shows the effects of Compounds 1 and 2 on keratinocyte detachment in comparison to ATRA.

Retinoid-Induced Skin Thickening.

Topical treatment of skin with ATRA results in keratinocyte proliferation, leading to enhanced epidermal thickening. Past studies have demonstrated that epidermal thickening can also be seen in organ-cultured human skin (see, e.g., Varani J, et al., J Clin Invest. 1994; 94:1747-1756; Varani J, et al., Am J Pathol. 1993 January; 142(1):189-98; Lateef H, et al., Am J Pathol. 2004; 165:167-174; Varani J, et al., Exp Mol Pathol. 2004; 77(3):176-83; Varani J, et al., Am J Pathol. 1993 June; 142(6):1813-22; Varani J, et al., *Toxicol. Pathol.* 35:693-701, 2007; Rittié L, et al., *J Invest Dermatol,* 126:732-739, 2006).

Figure 6A:
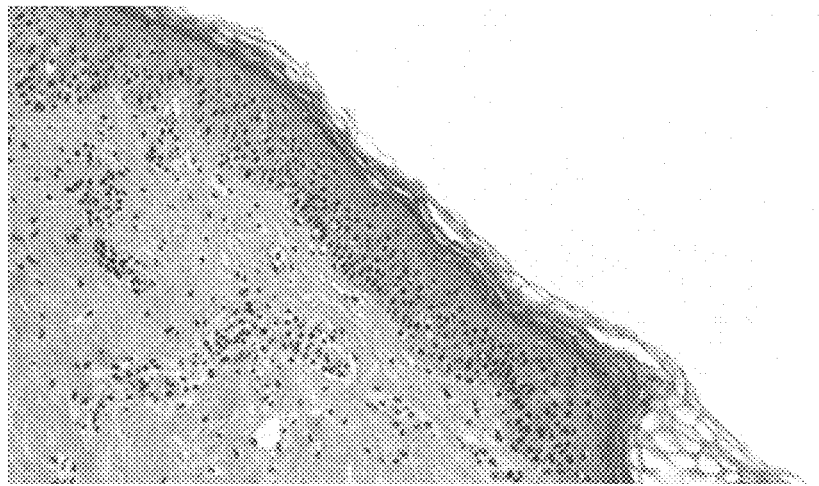
FIGS. 6A-C: Comparison of Example 1 and ATRA for ability to stimulate epidermal thickening in normal human skin in organ culture. Human skin biopsies were incubated for 8 days in organ culture. Biopsies were kept as control (KBM supplemented with 1.5 mM calcium) (6A) or treated with either ATRA (6B) or Example 1 (6C) (both at 1 µg/mL). At the end of the incubation period, the tissue was fixed for histology and examined at the light microscopy level after staining with hematoxylin and eosin. The control skin sample (6A) has the appearance of freshly biopsied human skin while both ATRA-treated skin (6B) and Ex. 1-treated skin (6C) demonstrate hyperplastic changes (increased epidermal thickening) that is a characteristic feature of retinoid-treated skin. In the ATRA-treated section, there is also evidence of toxicity in the upper epidermis (i.e., incomplete keratinization with loss of granular layer). These abnormalities are not seen in the ex. 1—treated skin section.
Figure 6B:
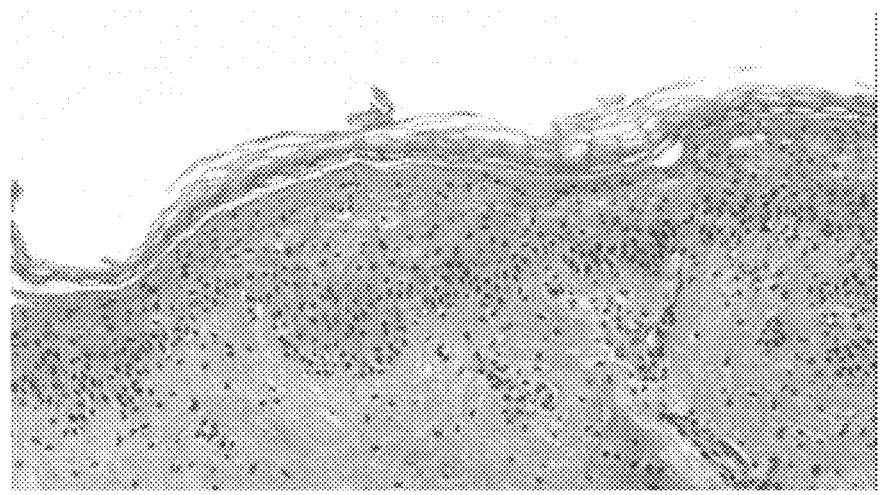
Figure 6C:
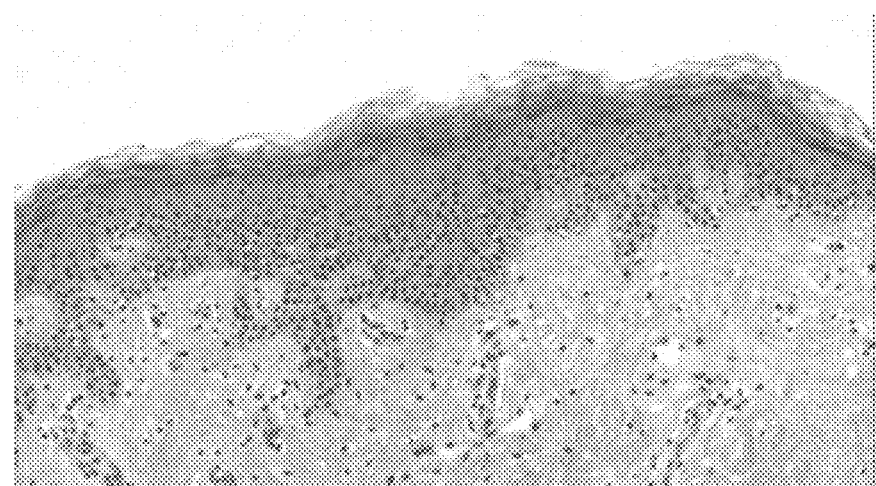

In these experiments, skin biopsies were obtained from normal volunteers and exposed the skin in organ culture to either ATRA (1 µg/mL) or Compound 1 at the same concentration. As shown in FIG. 6, both retinoids induced the expected hyperplastic changes.

B. Anti-Cancer Activity

Introduction.

All trans retinoic acid (ATRA) is a frontline treatment for all stages of acute promyelocytic leukemia (APL), 90% of which contain an RARa-PML fusion oncogene. It is efficacious, and APL is survived by 70-90% of patients. However, the side effects of ATRA treatment are many and common; symptoms include headache, fever, dry skin and mucous membranes, bone pain, nausea and vomiting, rash, mouth sores, itching, sweating, eyesight changes and a slew of other ills. While many of these are unpleasant, differentiation syndrome (DS) is potentially fatal and occurs in up to 30% of patients. It is managed with steroids, and by interrupting the course of treatment; hoping that the patient regresses on chemotherapy alone. While PML affects only a small number of individuals [about 2300 people per year in the U.S.], recent studies have also shown that 40% of all AML cases (those with the genetic mutation referred to as nucleeophosmin-1[NPM-1]) appear to be retinoid sensitive. Additionally, retinoids are also used in the treatment of other cancers, including neuroblastoma and hepatocellular carcinoma (7). As the first step in determining if any of the four experimental retinoids might be, the agents were screened for ability to suppress the proliferation of NB4 cells in culture. In parallel, we assessed cells for changes in size and shape that reflect differentiation Experimental Design.

Concentration-dependent and time-dependent growth inhibition studies were carried out in vitro. Cells were plated in wells of a 24-well dish at $5\times10^4$ cells per well in maintenance media (DMEM+2% fetal bovine serum. Each of the experimental retinoids were added at the desired concentrations and the cells incubated for 3 days. At the end of the incubation period, cells were counted using an electronic particle counter. Viability was determined by exclusion of trypan blue. To assess differentiation, cells were treated for three days with either the desired agent (or control) in culture medium. At the end of the incubation period, the cells were photographed under phase-contrast microscopy.

Results and Discussion.

Figure 7A:
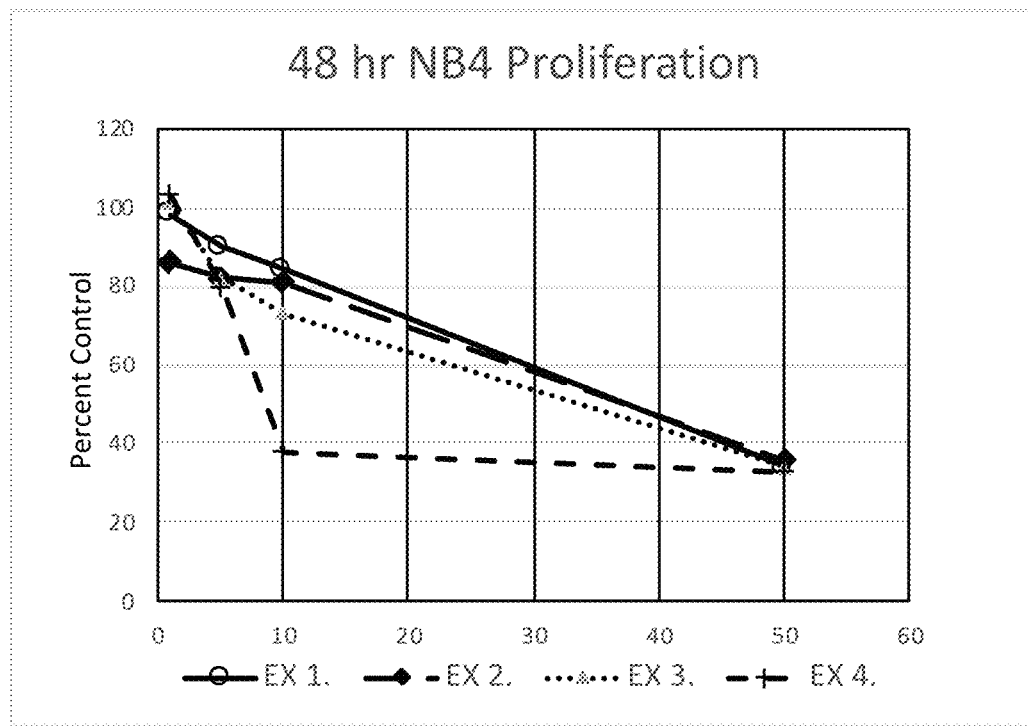
FIGS. 7A & FIG. 7B: Inhibition growth and induction of differentiation with NB4 cells (PML cell line) by experimental retinoids. Dose-dependent growth inhibition at 48 hours (7A) and at 72 hours (7B) over the range 1-50 µg/mL.
Figure 7B:
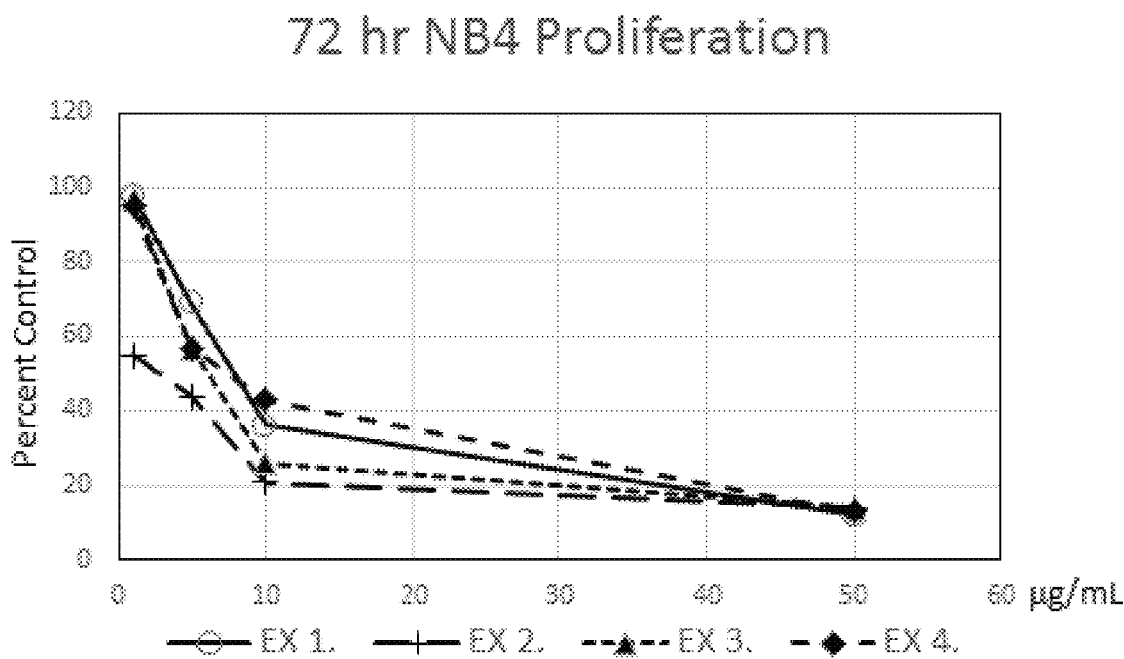
Figure 8A:
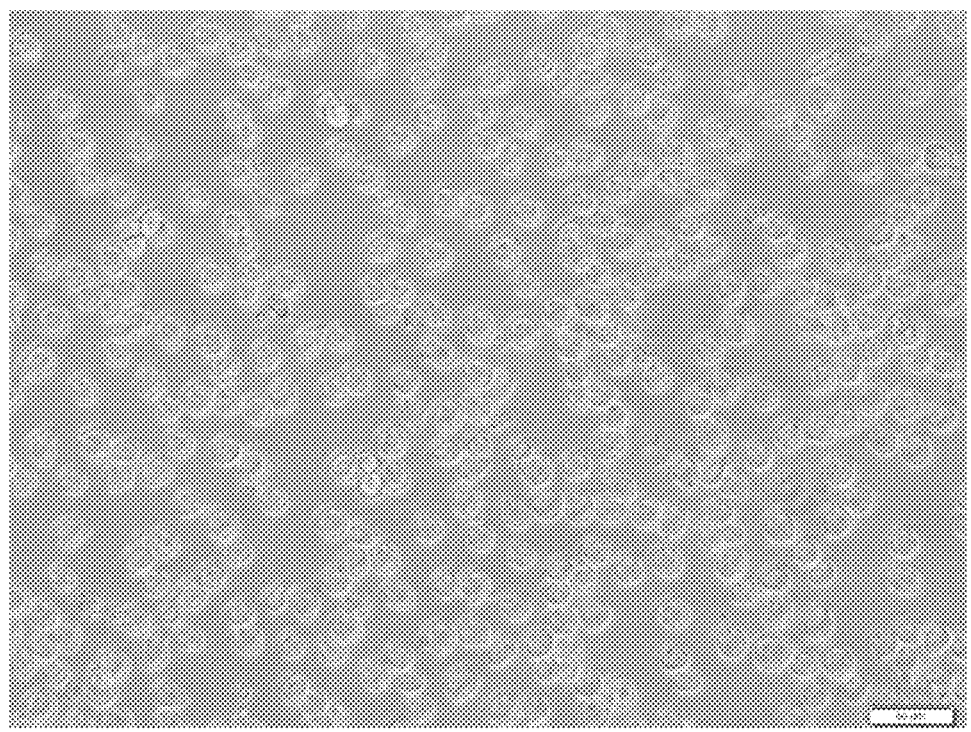
FIGS. 8A & FIG. 8B: Morphological change with Compound 2. Control NB4 cells are shown after 48 hours incubation in culture medium in FIG. 8A.
Figure 8B:
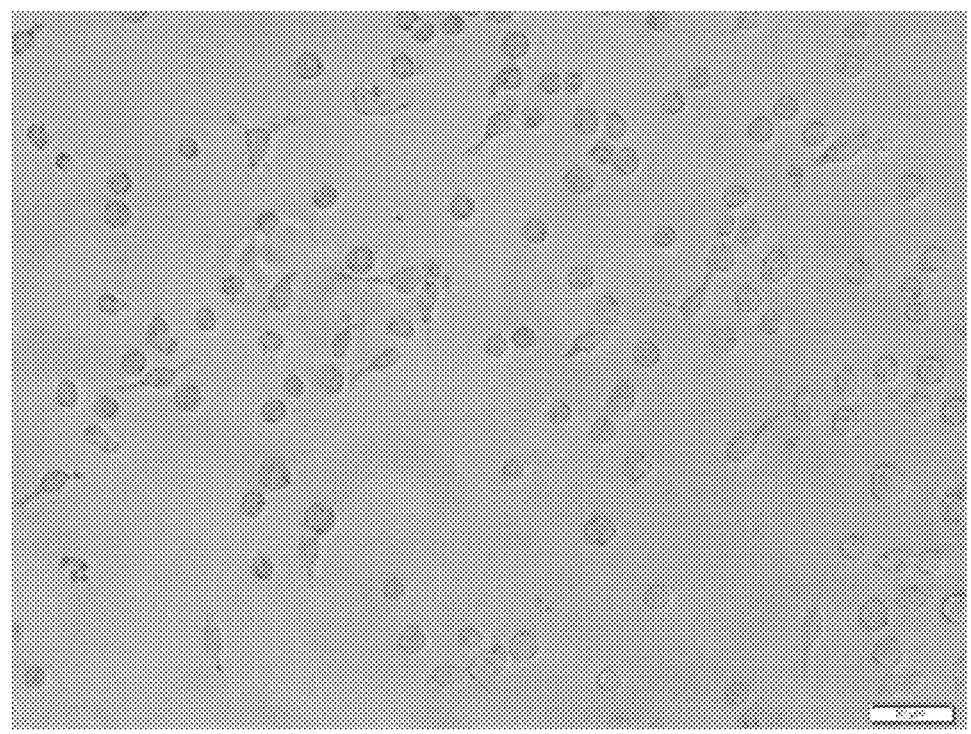
Figure 9A:
FIGS. 9A-D: Comparison of Examples 1 & 2 and ATRA in the rhinomouse, a model for acnegenesis. Adult rhino mice were either treated topically with 100 µL of vehicle control (DMSO), or 100 µL of the appropriate concentration of, Example 1 or Example 2 in DMSO or 35 mg of 0.1% ATRA cream, daily for 21 days, and photographed on Day 22. Control animals (as exemplified in 9A have a normal rhino mouse appearance, as do animals dosed with Examples 1 & 2 (9C and 9D). However, animals dosed with ATRA, (9B) show considerable skin irritation, along with excessive skin flaking.
Figure 9B:
Figure 9C:
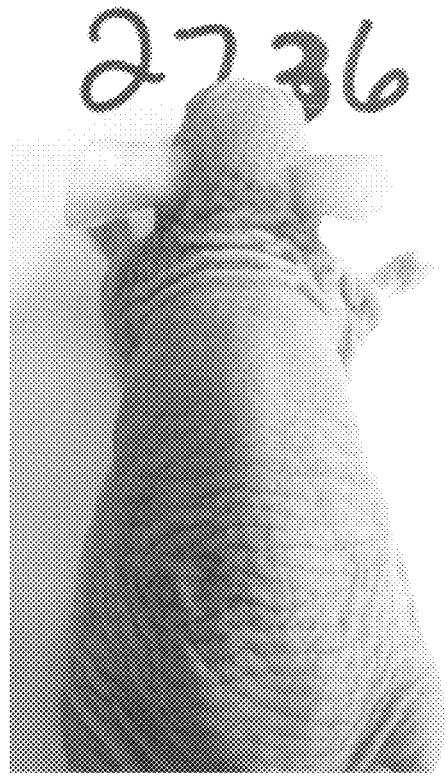
Figure 9D:
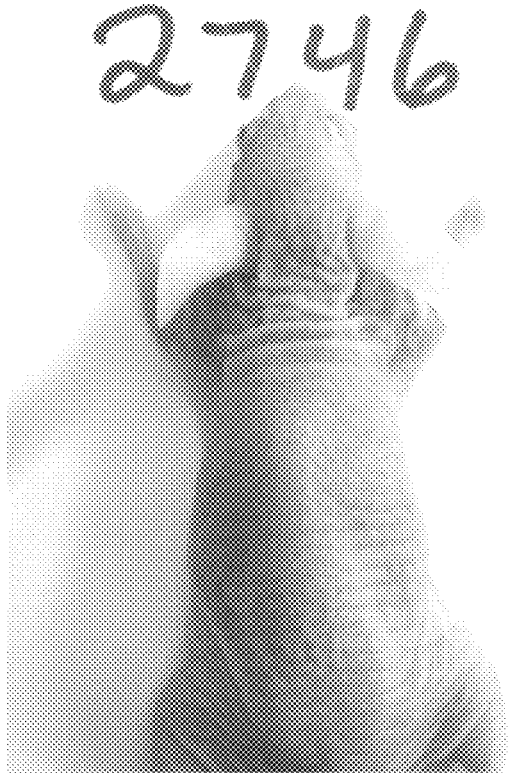

Results of this study are shown in FIGS. 7 and 8. FIG. 7 demonstrates that all four agents produced a comparable, concentration-dependent growth inhibition with the test PML cell line, over the range 1-50 µg/mL. Inhibition could be seen at both 48 and 72 hours of incubation. FIG. 8 shows phase contrast images of untreated and Compound 2 (50

µg/mL) treated NB4 cells. As can be seen in the figure, a change in morphology from round (control cells; upper image) to polarized and flattened (Compound 2-treated, lower image) was clearly visible in some of the retinoid-treated NB4 cells. The polarized, flattened morphology is evidence of differentiation. These studies, thus, indicate that the experimental retinoids have potential as anti-cancer agents.

Example 6. In Vivo Assays for Anti-Acne Activity in Rhinomouse

Introduction.

The rhinomouse model is an industry-standard pre-clinical model for evaluation of retinoids for anti-acne activity. The mice can be treated topically over a course of days with the desired compound (either formulated or in liquid solvent). During the course of treatment, the animals can be evaluated grossly for skin irritation. At the end of the treatment phase, the animals are euthanized. Skin from treated sites can be evaluated for efficacy—reduction in the number of horn-filled utriculi—and for histological evidence of inflammation.

Experimental Design.

Mice.

Rhino mice (HRS\J $hr^{rh}hr^{rh}$)) were obtained from Jackson Laboratories. Animals were recent weanlings; at this stage in the life of the rhinomouse, the phenotype (i.e., skin with numerous horn-filled utriculi) is well expressed and continues to be for several weeks. Both males and females were included. Animals were divided into treatment groups. Once in the laboratory, the mice were kept in temperature- and humidity-controlled rooms. All procedures during the in-life portion of the study were carried out in facilities of the Unit for Laboratory Animal Medicine (ULAM) at the University of Michigan—which is an AAALAC-certified institution. All procedures were carried out with approval by the University of Michigan Institutional Animal Care and Use Committee (IACUC).

Test Articles.

Each of the 4 experimental retinoids was made up in DMSO as 0.1% and 0.3% solutions. The material was applied to the treatment area (2 $cm^2$ area) on a dot marked area on the inter-scapular back) once daily for 7 consecutive days or for 21 consecutive days. The test agent was gently rubbed into the test site after application. As a control, Tretinoin-0.1% was used. Tretinoin-0.1% contains all-trans retinoic acid (ATRA) as active agent at a final concentration of 0.1%. This is a commonly-prescribed anti-acne medicine. A set amount of the test article, DMSO, DMSO plus test drug, or Tretinoin cream (35 mg) was delivered using a Gilson MICROMAN fully adjustable positive placement pipette. It should be noted that if the ATRA was delivered in the same quantities as a DMSO solution it would be considerably more powerful an irritant.

Evaluations.

Animals were housed individually during the treatment phase of the study. During the treatment phase, animals were assessed daily for overall health, and for signs of skin irritation. The Draize scale was used to assess skin irritation. The Draize scale evaluates the parameters of erythema and edema. Each parameter was scored between 0 and 4+ with 0 indicating no difference from control mice and 4+ indicating maximum erythema or edema. In addition, animals were assessed for dryness/flaking/cracking (single score). The overall irritation score was a compilation of the three parameters in all mice from a treatment group. During the treatment phase, animals were weighed weekly.

Necropsy and Histological Analysis.

One day after the last treatment, animals were euthanized. The animals were injected with 7 ml 10% buffered formalin after euthanasia. 15 minutes later the treated area on the back of the mouse was removed and cut into 8 pieces. Every other piece was taken, so four pieces of skin were mounted in one cassette and fixed for histology. An extra piece of skin from a non-treated area was also evaluated.

Epidermal Thickness:

Hematoxylin and eosin stained sections were evaluated microscopically for epidermal thickness with measurements made in the inter-follicular regions at 4 representative sites per tissue strip.

Horn-Filled Utriculi:

The number of horn-filled utriculi was determined by direct counting in the entire section of skin. Each of the four sections per biopsy was used for determining the number of utriculi. Section lengths were measured as a way to normalize findings. Typically, the section of skin varied from 16-20 mm.

Inflammation:

Slides were examined microscopically and inflammation was scored on a 0 to 4+ basis. A score of zero indicated no inflammation while increasing collection of inflammatory cells was identified with increasing score. Slides were also evaluated to determine if inflammation was confined to the dermis or whether there was epidermal inflammation. Dermal inflammation was assessed to determine if inflammatory cells were scattered throughout the dermis or whether small abscesses were also present. Finally, the inflammatory lesions were evaluated to determine whether they consisted of primarily mononuclear cells, granulocytic cells or both. A similar scale has been used previously in the assessment of skin irritation.

Results.

All animals arrived from the vendor in a healthy condition. The mice remained healthy until the start of the treatment phase.

Gross Findings During in-Life Portion of Study.

FIG. 1 left provides a summation of the skin irritation response in the different treatment groups. In control mice, there was little evidence of skin irritation at any time throughout the study. Beginning on day-3 of treatment, signs of irritation could be seen in animals exposed to Tretinoin (ATRA). The initial spike in irritation was followed by a dip and then secondary rise. This is consistent with what is typically seen with ATRA. As compared to control, the experimental retinoids also demonstrated skin irritation. However, the degree of irritation was much lower than that observed with ATRA. FIG. 9 shows examples of mice from the control group (upper left), the ATRA-treated group (upper right) and Compounds 1 and 2 (lower left and right respectively). Neither the control mouse nor the Compound 1 & 2 treated mice show visible signs of irritation in the skin. In contrast, skin from the ATRA-treated mouse is red, dry and flaky. Small cracks in the skin can be seen and there is significant edema. FIG. 10 illustrates that Compound 2 at doses of 0.1% and 0.3% did not show any signs of serious skin irritation at either dose.

Figure 11:
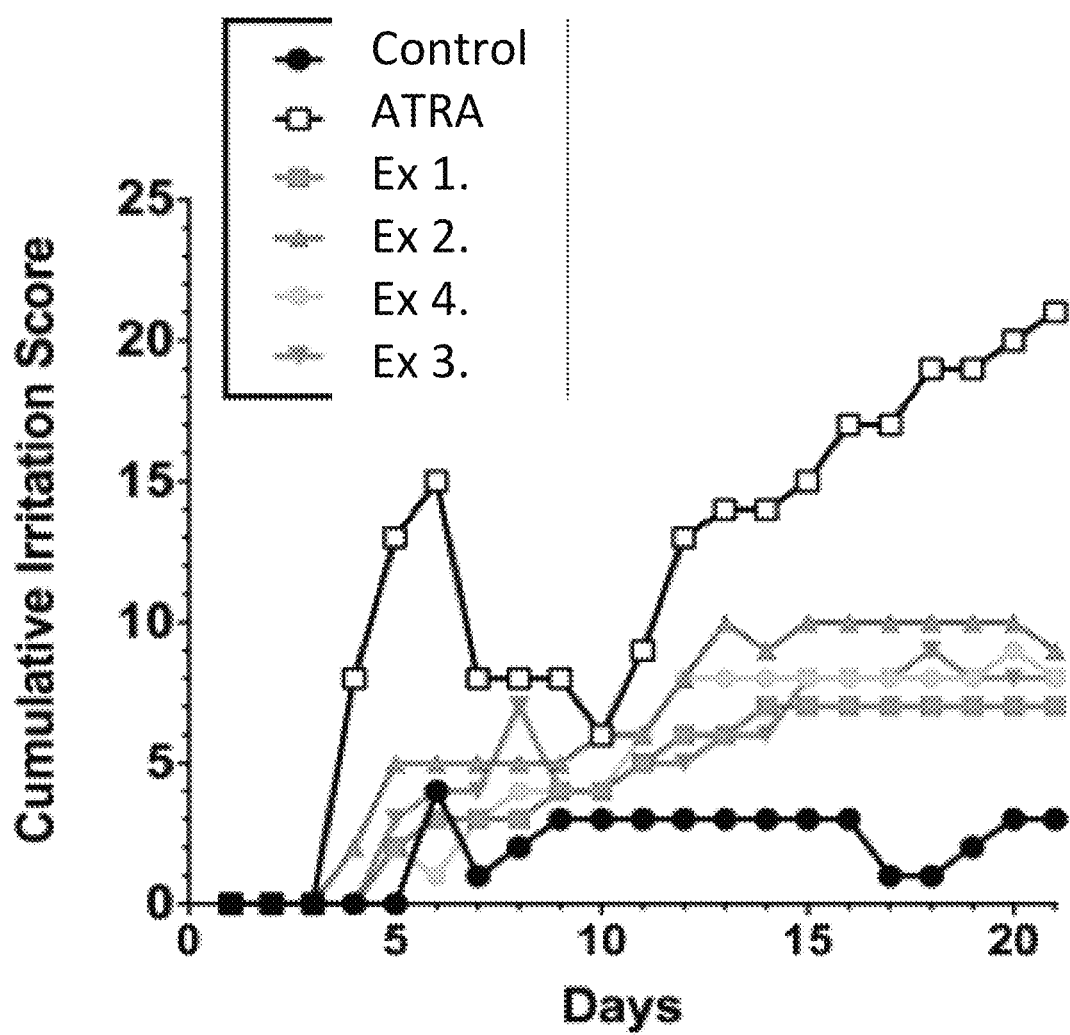
FIG. 11. This graph shows skin irritation over the course of topically dosing the rhino mouse with Examples 1-4 at 0.1% daily for 21 days, along with ATRA at 0.1% and DMSO control. The cumulative irritation score is a modified version of the Draize irritation scale, and the animals were assessed daily by an assessor who was blinded to the treatment given each mouse. The quick flare up with ATRA, followed by partial recovery, with a rebound irritation is very typically seen with ATRA in this model.

The results of the "Cumulative Irritation Score" study are shown in FIG. 11. Although increased irritation was noted with Examples 1-4, it can be seen that ATRA was far more irritant, and showed a typical initial flare followed by partial resolution, and a continual deterioration through the end of the dosing period. In contrast. Examples 1-4 all showed stable, and lower irritation scores after two weeks.

Animals were weighed weekly during the course of study. The results below are for animals treated with 0.1% formulations of the test drug. Control animals gained an average of 0.85±0.47 grams over the course of treatment (21 days) while animals treated with ATRA lost an average of 1.63±1.09 grams. The loss of weight during ATRA treatment (in mice) is expected. Animals treated with the experimental retinoids did not lose weight. Compound 1 treated animals gained 1.30±0.92 grams; Compound 2—treated mice gained 1.48±0.25 grams; Compound 3—treated mice gained 1.90±1.28 grams and Compound 4—treated mice gained 1.40±0.34 grams.

Euthanasia and Terminal Analysis.

Figure 12A:
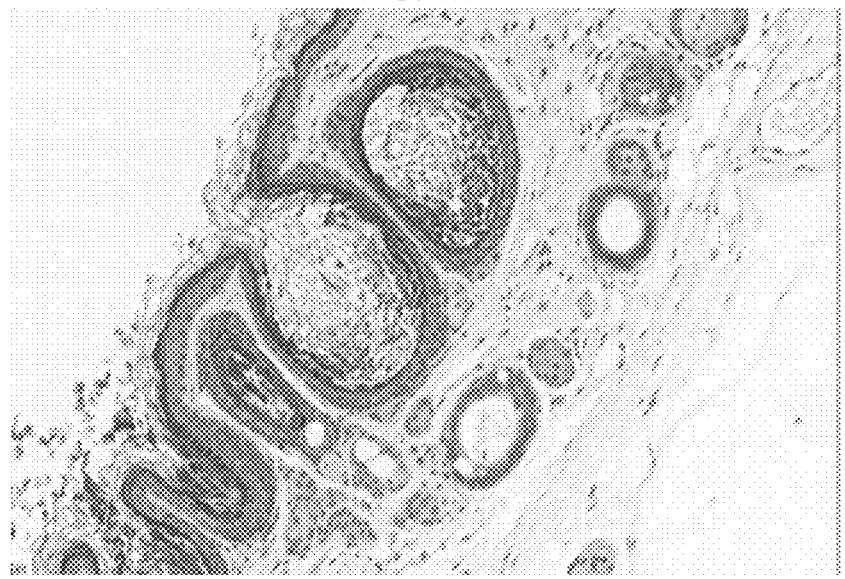
FIGS. 12A-C: Efficacy of retinoids at normalizing structure of rhino mouse skin after topical treatment for 21 days.
Figure 12B:
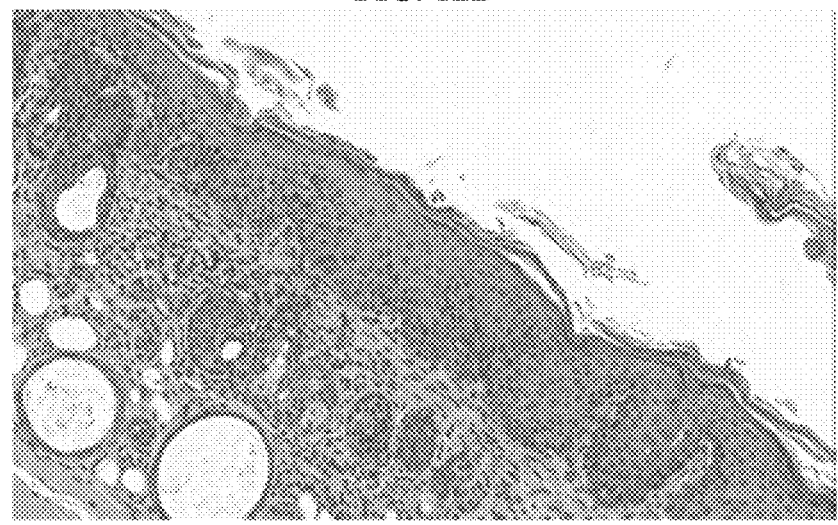
Figure 12C:
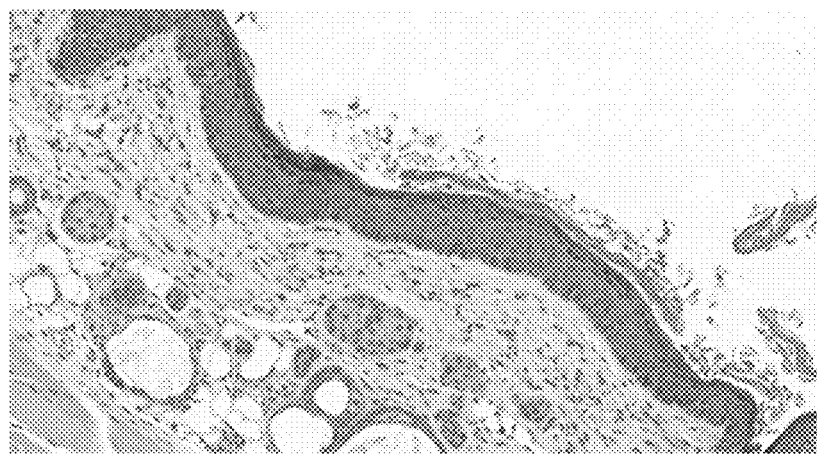
Figure 13A:
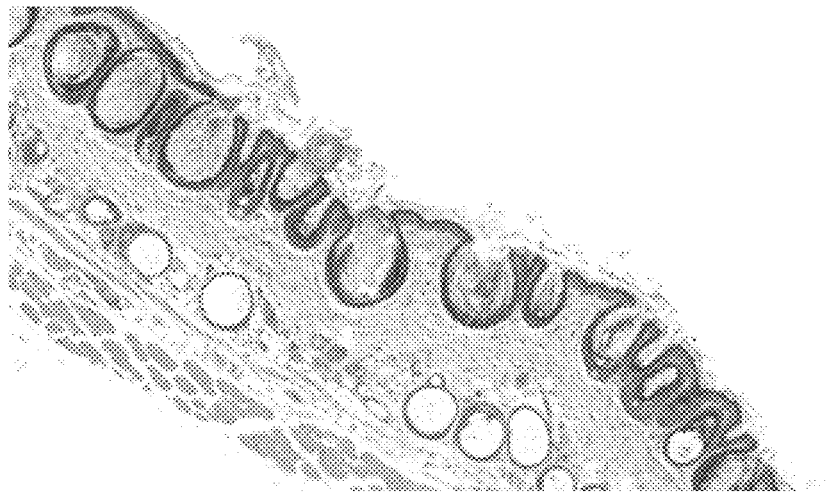
FIGS. 13A-C: Dose related effect of Example 2 on rhino mouse skin.
Figure 13B:
Figure 13C:
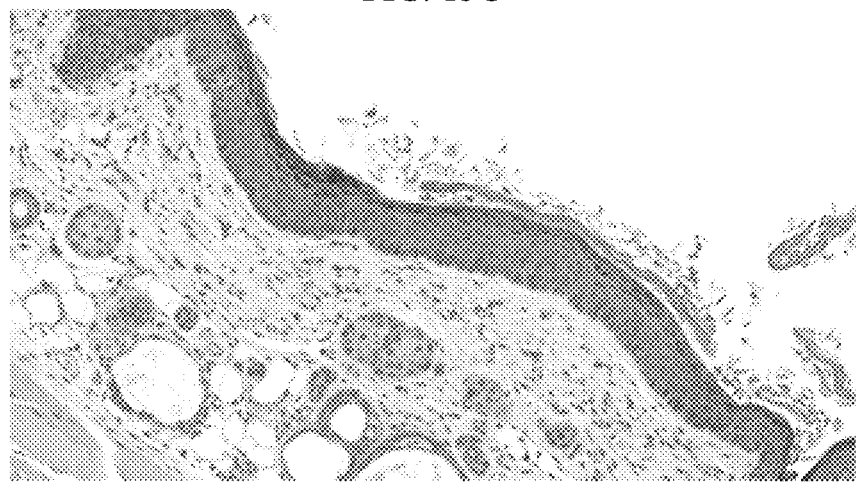

At the end of the in-life portion of the study, mice were euthanized by $CO_2$ overdose. Hematoxylin and eosin-stained histological sections from each mouse in the control, ATRA-treated and Compound 2-treated groups were evaluated with regard to the number of horn-filled utriculi, epidermal thickness, and inflammation. The results are summarized in Table 2 and representative images are shown in FIG. 2. Briefly, the epidermis of control mice consisted of a thin epidermis with large numbers of horn-filled utriculi (98+10 per 20 mm of epidermal linear length). Both retinoids almost completely suppressed utriculi formation while substantially increasing epidermal thickness. While Compound 2 was similar to ATRA in terms of utriculi-reduction, the two retinoids were different in regard to inflammation. ATRA treatment produced a much higher inflammation "score" (Table 3). This is evident from the histological sections presented in FIG. 12. The histological section from the control mouse (top left) shows the thin skin and utriculi typical of the phenotype. Both the ATRA-treated mouse (top right panel) the Compound 2 treated skin (bottom panel) show both much thickened dermis and disappearance of utriculi. However ATRA, in sharp contrast to Compound 2 demonstrates an intense inflammatory cell infiltrate. There were large numbers of inflammatory cells in the dermis. Microabscesses could be seen in places, and migration of inflammatory cells into the epidermis was also evident. The infiltrate consisted of both mononuclear cells and granulocytes. In contrast, the histological section from the Compound 2-treated mouse (lower-left panel) showed little inflammatory cell infiltrate. The three other experimental retinoids were also examined along with Compound 2. Compounds 1, 3 & 4 also reduced the number of utriculi as compared to control, and, like Compound 2, did not produce an inflammatory response or induce a rise in the pro-inflammatory cytokine level (Table 3). In FIG. 13 it can be seen that during the dosing period 0.1% of Compound 2 led to skin thickening, but incomplete resolution of the utricali, whereas at 0.3% the utricali were more fully resolved.

TABLE 2

ATRA and Compound 2 treatment of rhinomouse.

| Utriculus number | |
| --- | --- |
| Control | 98 ± 10 |
| ATRA | 2 ± 2 |
| Ex. 2 (0.1%) | 7 ± 5 |
| Ex. 2 (0.3%) | 5 ± 3 |
| Epidermal thickness | |
| Control | 14 ± 7 |
| ATRA | 68 ± 17 |

TABLE 2-continued

ATRA and Compound 2 treatment of rhinomouse.

| Ex. 2 (0.1%) | 45 ± 8 |
| --- | --- |
| Ex. 2 (0.3% | 44 ± 6 |
| Inflammatory index | |
| Control | 0.2 ± 0.2 |
| ATRA | 3.3 ± 1.5 |
| Ex. 2 (0.1%) | 1.1 ± 0.6 |
| Ex. 2 (0.3%) | 0.9 ± 0.4 |

Serum was obtained from all mice at the end of the study and evaluated for levels of pro-inflammatory cytokines. For this, the same multiplex ELISA used with human samples was employed except that mouse-recognizing antibodies replaced antibodies used to detect the human counterparts. As seen in Table 3, there was an increase in levels of MCP-1, IL-6 and KC/IL-8 in serum from ATRA-treated mice. Cytokine values from mice exposed to the experimental retinoids were no higher than levels in serum from control mice—or actually lower.

TABLE 3

Rhinomouse Studies: Serum cytokine levels in retinoid-treated mice.

| Treatment Group | MCP-1 | IL-6 | KC/IL-8 | IL-1β | TNF-α |
| --- | --- | --- | --- | --- | --- |
| Control | 76 ± 30 | 0.51 ± 0.61 | 17 ± 4 | low | low |
| ATRA | 158 ± 43 | 1.55 ± 0.66 | 23 ± 4 | low | low |
| (0.1% Tretinoin) | | | | | |
| Ex. 1 | | | | | |
| 0.1% | 53 ± 19 | 0.29 ± 0.17 | 20 ± 3 | low | low |
| 0.3% | 52 ± 26 | 0.09 ± 0.12 | 12 ± 5 | low | low |
| Ex. 2 | | | | | |
| 0.1% | 65 ± 30 | 0.17 ± 0.14 | 20 ± 2 | low | low |
| 0.3% | 63 ± 20 | 0.03 ± 0.03 | 12 ± 3 | low | low |
| Ex. 3 | | | | | |
| 0.1% | 52 ± 7 | 0.15 ± 0.09 | 17 ± 2 | low | low |
| 0.3% | 16 ± 8 | 0.03 ± 0.06 | 13 ± 5 | low | low |
| Ex. 4 | | | | | |
| 0.1% | 45 ± 11 | 1.19 ± 0.59 | 18 ± 5 | low | low |
| 0.3% | 45 ± 18 | 0.19 ± 0.11 | 16 ± 3 | low | low |

Values are means ± sd in pg/mL based on 4-8 mice per group

Figure 14:
FIG. 14: Spleen sizes of rhino mice dosed topically with DMSO (control) and 0.1% of ATRA or Examples 1-4 compounded in DMSO for 21 days. Only ATRA produces the increase in spleen size typical of immune system activation.
Figure 16:
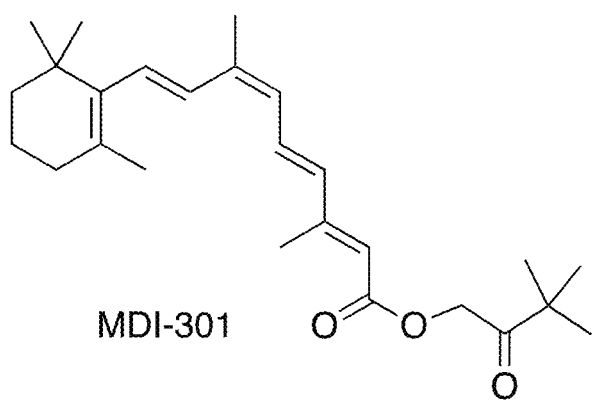
FIG. 16: Structure of MDI 301.

Mouse skin is rather thinner than human skin, and topically applied drugs tend to get into the circulation more readily when applied to mice, especially the hairless mutants, than to humans. FIG. 14 shows the spleen sizes of animals dosed with control, ATRA and Examples 1-4. ATRA shows very marked splenomegaly, a typical finding for pro-inflammatory retinoids, whereas Examples 1-4, show very modest splenomegaly, suggesting little systemic immune system activation.

Discussion.

Taken together, these findings demonstrate that the experimental retinoids that are the subject of this patent have efficacy in the rhinomouse model for anti-acne activity but do not induce skin irritation. Based on the histological findings, cytokine data and lack of weight loss, these data show that anti-efficacy can be seen in the absence of an intense inflammatory response.

Example 7

This example demonstrates the ability of MDI 301 to treat skin-wounds.

MDI 301 is a pinacolone ester derivative of 9-cis retinoic acid developed by Molecular Design International (MDI) (Memphis, Tenn.). Past studies demonstrated that MDI 301 is similar to all-trans retinoic acid (ATRA) for skin repair. That is, in a human skin organ culture model, both retinoids induced procollagen I production and inhibited the major collagen-degrading enzyme (MMP-1, collagenase 1). Beneficial effects with MDI 301 have been observed in mice, rats, rabbits, Göttingen minipigs and human skin in organ culture (see, e.g., Varani J, et al., Arch. Dermatol. Res. 295:255-262, 2003; Appleyard VCL, et al., Anticancer Res. 15:991-996, 2004; Varani J, et al., Arch. Dermatol. Res. 298:439-448, 2007; Warner R L, et al., Wound Repair Regen. 16:117-124, 2008; Dame M K, et al., In Vitro Cell. Dev. Biol. Anim. 2009; 45(9):551-557). Although MDI 301 was comparable to ATRA in stimulating procollagen production and inhibiting collagen-degrading MMP-1, MDI 301 was unlike ATRA in that it did not up-regulate the pro-inflammatory cytokines that underlie retinoid-induced skin irritation whereas ATRA, as expected, did. Further in vivo studies have demonstrated that even intraperitoneal dosing of MDI 301 did not elicit systemic cytokine release whereas ATRA did (see, e.g., Aslam M N, et al., Anti-Cancer Drugs 2015, 26:763-773).

Given the lack of irritation associated with MDI 301, experiments were conducted reasoning that this retinoid might work in the acute wound setting. To test this idea, experiments were conducted as shown in FIG. 15. Essentially, a group of rats were treated with a potent steroid to induce skin atrophy followed by a wounding of the skin. Following this, rats were treated with vehicle alone or with MDI 301. As shown in FIG. 15, skin wounds healed more rapidly in the retinoid-treated rats than in control rats. The top right and left panels (A) show the original wound, and the second row shows the animals after 13 days of daily dosing of the wound periphery with ~100 mgs of 1.0% containing MDI 301 cream. The third row of panels shows the histology of the wounded skin after 13 days. It should be noted that in this study ATRA cannot be used, as its irritant properties exacerbate the original injury.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

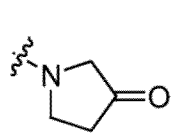 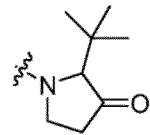 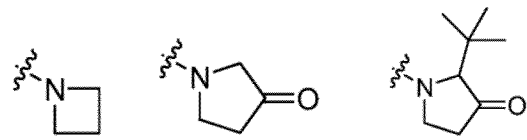

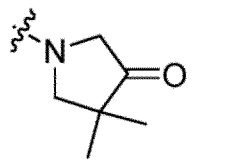 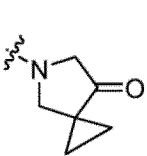

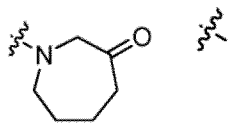 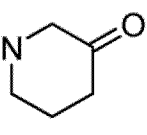

What is claimed is:
1. A compound having Formula I:

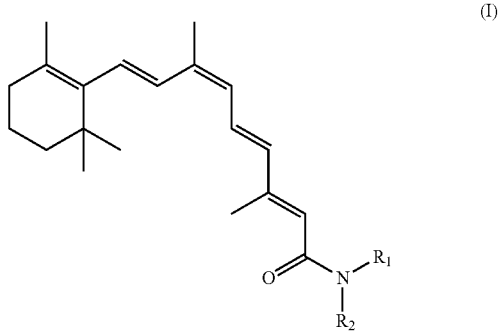

or a pharmacologically acceptable salt, or a hydrate, or a solvate, or prodrug, thereof; wherein
$R_1$ is $CH_3$, $CF_3$, $C_{2-10}$ alkyl, $C_{3-10}$ alkenyl, $C_{3-10}$ alkynyl, all of which may be straight chain or branched, or $CF_3$, which can be optionally substituted with up to three groups chosen independently from $C_{1-10}$ alkyl, $C_{3-10}$ cycloalkyl, $C_{2-10}$ alkenyl $C_{3-10}$ cycloalkenyl, $C_{2-10}$ alkynyl, wherein all aliphatics may be straight chain or branched, halogen, hydroxy, cyano, oxo, $CF_3$, $OR_4$, or $OR_3$; and independently;
$R_2$ is $CH_2(CO)R_3$, $C_{1-10}$ alkyl, $C_{3-10}$ alkenyl, $C_{3-10}$ alkynyl, all of which may be straight chain or branched, or $CF_3$, which can be optionally substituted with up to three groups chosen independently from $C_{1-10}$ alkyl, $C_{3-10}$ cycloalkyl, $C_{2-10}$ alkenyl $C_{3-10}$ cycloalkenyl, $C_{2-10}$ alkynyl, wherein all aliphatics may be straight chain or branched, halogen, hydroxy, cyano, oxo, $CF_3$, $OR_4$, or $OR_3$;
or $R_1$ and $R_2$, along with the nitrogen both are bonded to form an optionally substituted ring having from 4-7 atoms, wherein the optionally substituted ring having from 4-7 atoms is selected from the group consisting of:

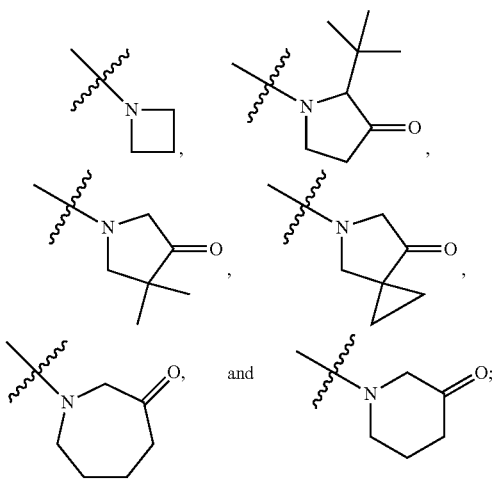

R₃ is C₂₋₁₀ alkyl, C₂₋₁₀ alkenyl, C₂₋₁₀ alkynyl, all of which may be straight chain or branched, phenyl, monocyclic or bicyclic 5-10 membered heteroaryl containing up to four heteroatoms chosen from N, O and S, C₃₋₇ cycloalkyl, 4-7 membered heterocycloalkyl, optionally substituted with up to three groups chosen independently from C₁₋₁₀ alkyl, C₃₋₁₀ cycloalkyl, C₂₋₁₀ alkenyl C₃₋₁₀ cycloalkenyl, C₂₋₁₀ alkynyl, C₃₋₁₀ branched alkyl, C₃₋₁₀ branched alkenyl, C₄₋₁₀ branched alkynyl, C₂₋₅ spiroalkyl, halogen, hydroxy, carboxy, cyano, oxo, or CF₃;

R₄ is selected from the group consisting of:

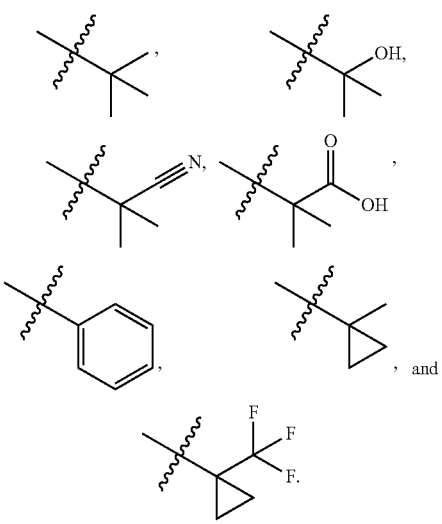

2. The compound according to claim 1, wherein the compound is selected from the group consisting of:

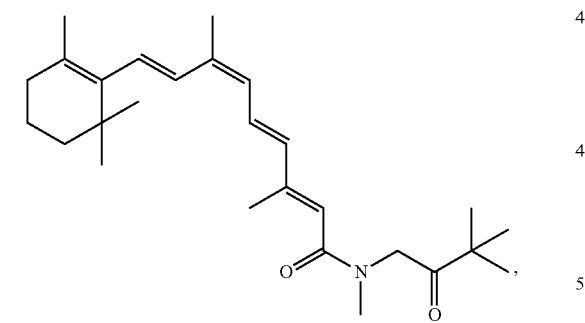

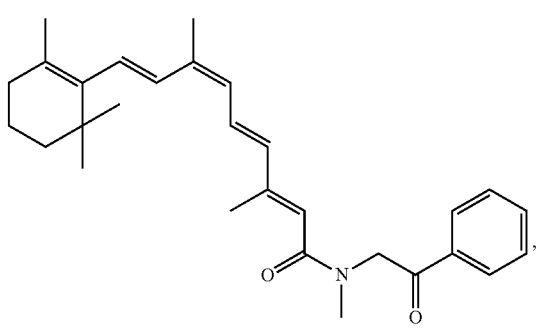

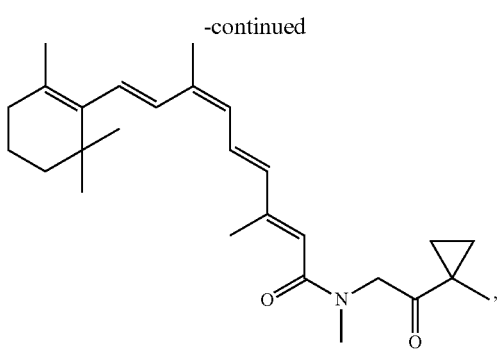

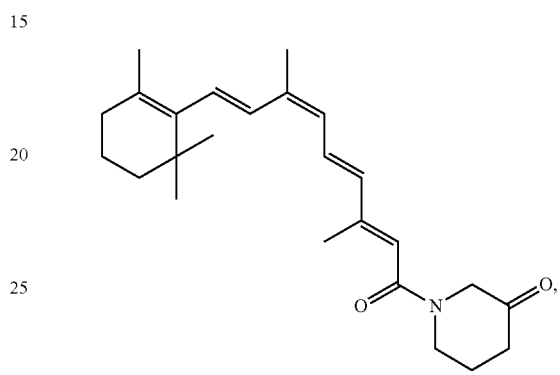

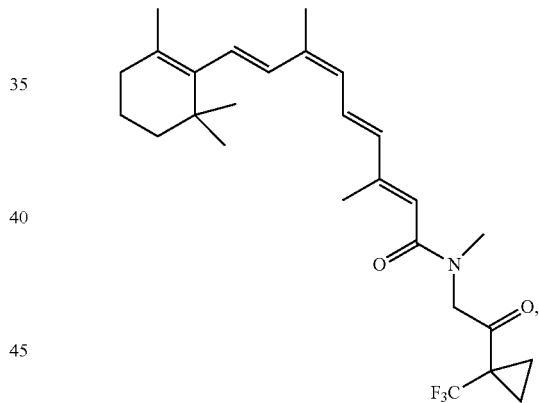

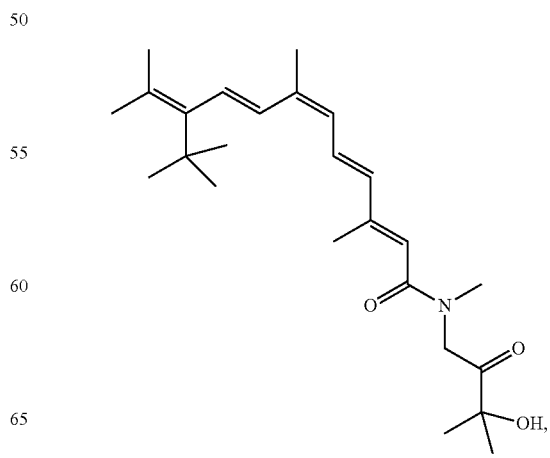

-continued

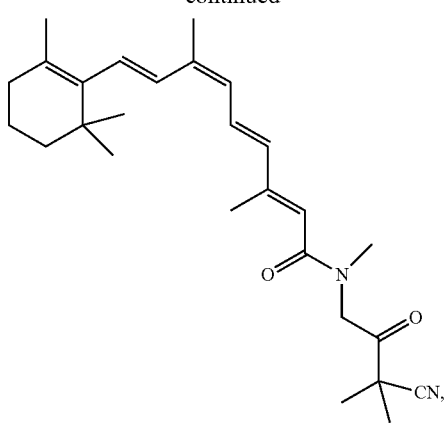

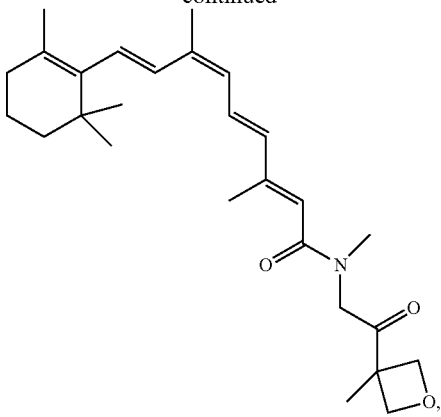

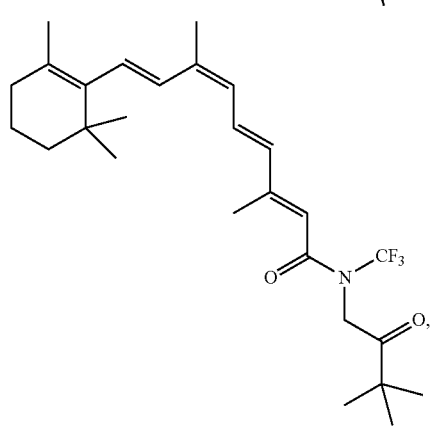

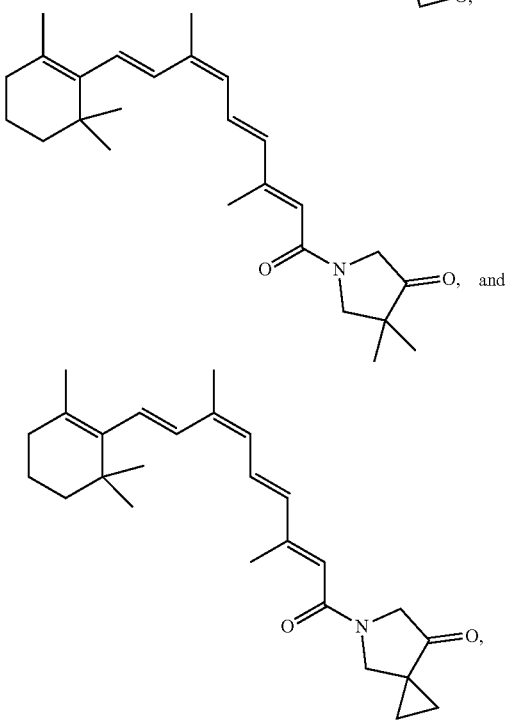

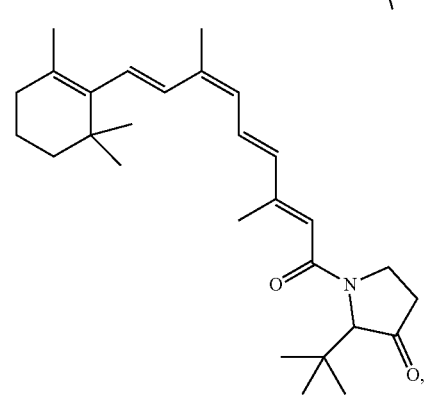

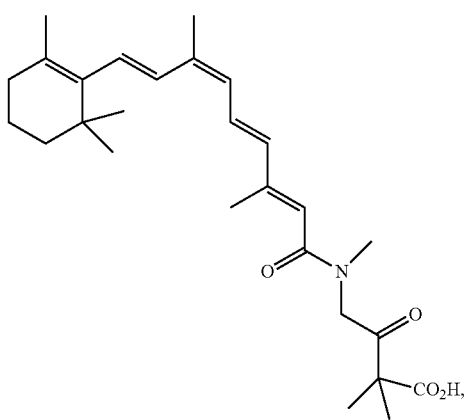

or a pharmaceutically acceptable salt, or solvate, or hydrate or prodrug.

3. The compound according to claim 1, in combination with a pharmaceutically acceptable composition.

4. A kit comprising a compound of claim 1 and instructions for administering said compound to a patient having an oncological disorder and/or a dermatological disorder,
   wherein the oncological disorder is selected from group consisting of acute promyelocytic leukemia (APL), neuroblastoma, head- and neck cancer, lung cancer, breast cancer, uterine cervix cancer, gastrointestinal tract cancer, skin cancer, bladder cancer and prostate cancer and similar disorders,
   wherein the dermatological disorder is selected from the group consisting of keratinization disorders such as rosacea, acne, psoriasis, severe psoriasis, lamellar ichthyosis, plantar warts, callosities, acanthosis *nigricans*, lichen planus, molluscum, melasma, corneal epithelial abrasion, geographic tongue, Fox-Fordyce disease, cutaneous metastatic melanoma and keloids, epidermolytic hyperkeratosis, Darier's disease, *pityriasis rubra pilaris*, congenital ichthyosiform erythroderma, hyperkeratosis palmaris et plantaris, melasma, hyperpigmentation and similar disorders.
5. The kit of claim 4, further comprising one or more anticancer agents.
6. A compound selected from the group consisting of:
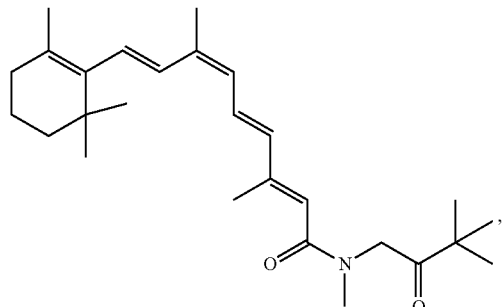
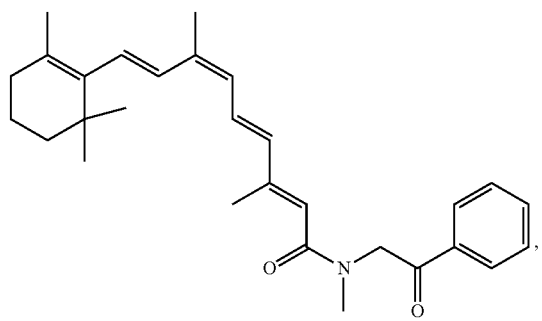
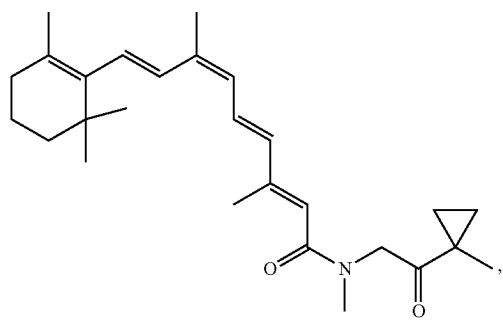
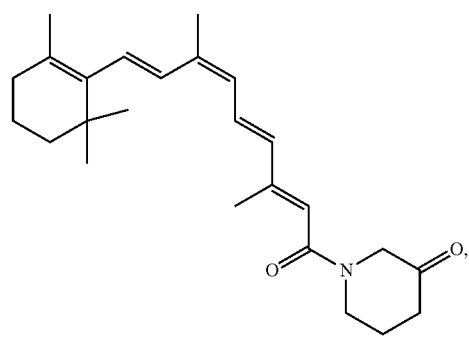
-continued
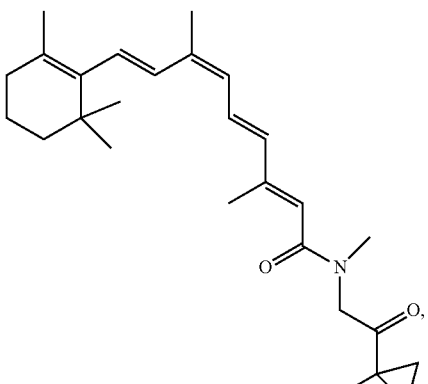
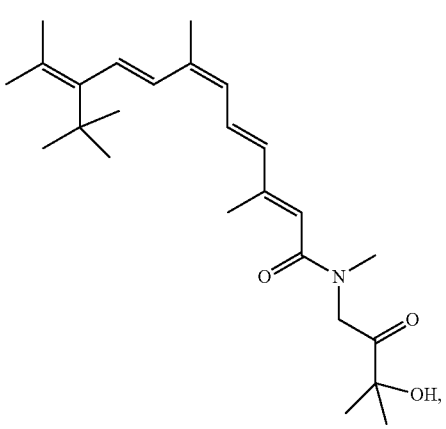
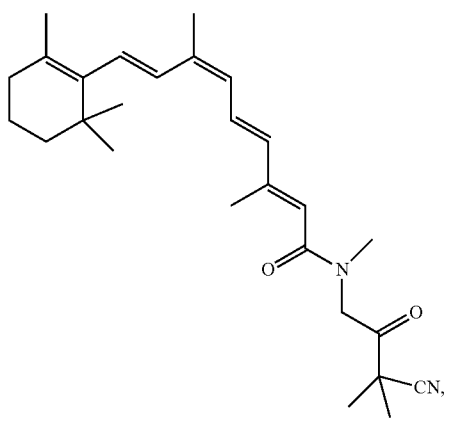
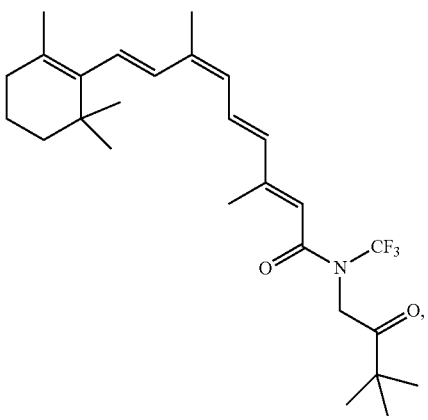

-continued

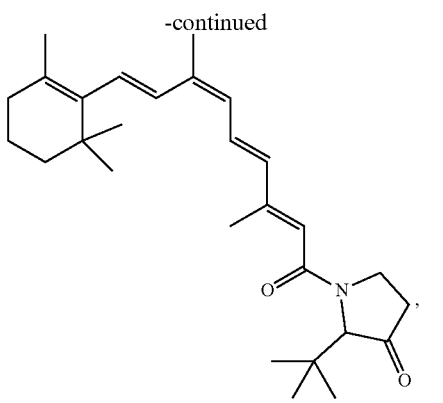

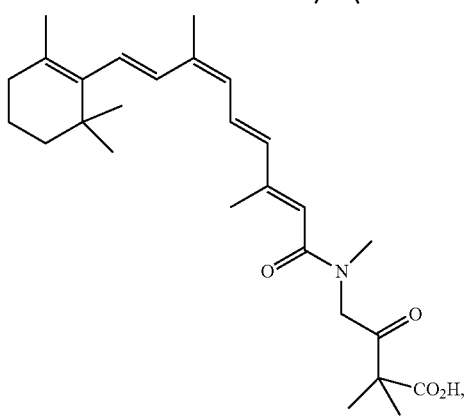

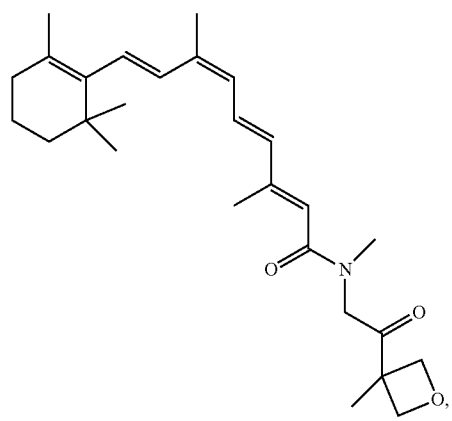

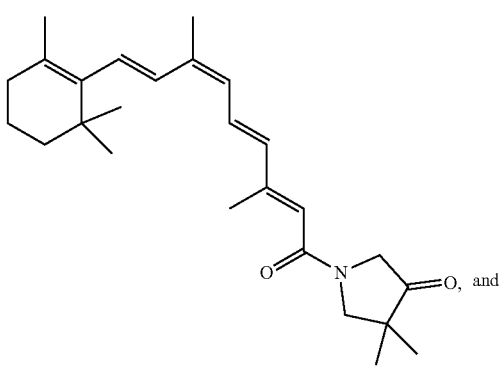

-continued

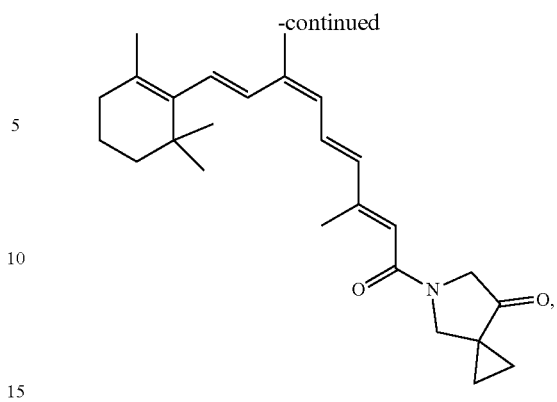

or a pharmaceutically acceptable salt, or solvate, or hydrate or prodrug thereof.

7. A method of treating, or ameliorating, disorders characterized by abnormal proliferation and/or abnormal differentiation of cells in a patient comprising administering to said patient a therapeutically effective amount of the pharmaceutical composition of claim 3,
wherein said disorder is an oncological disorder or a dermatological disorder,
wherein said patient is a human patient.

8. The method of claim 7, wherein the oncological disorder is selected from group consisting of acute promyelocytic leukemia (APL), neuroblastoma, head and neck cancer, lung cancer, breast cancer, uterine cervix cancer, gastrointestinal tract cancer, skin cancer, bladder cancer and prostate cancer and similar disorders.

9. The method of claim 8, wherein the oncological disorder is APL or neuroblastoma.

10. The method of claim 8, further comprising administering a second drug to said patient, wherein the second drug is one or more anticancer agents, wherein said anticancer agent is a chemotherapeutic agent or a radiation therapy or both.

11. The method of claim 7, wherein the dermatological disorder is selected from the group consisting of keratinization disorders epidermolytic hyperkeratosis, Darier's disease, *pityriasis rubra* pilaris, congenital ichthyosiform erythroderma, hyperkeratosis palmaris et plantaris, melasma, hyperpigmentation, and skin damage.

12. The method of claim 11 wherein the dermatological disorder is acne.

13. The method of claim 11 wherein the dermatological disorder is pressure ulcers/bedsores.

14. The method of claim 11 wherein the dermatological disorder is diabetic ulcers.

15. The method of claim 11 wherein the dermatological disorder is skin made atrophic by aging.

16. The method of claim 11,
wherein the keratinization disorders are selected from rosacea, acne, psoriasis, severe psoriasis, lamellar ichthyosis, plantar warts, callosities, acanthosis *nigricans*, lichen planus, molluscum, melasma, corneal epithelial abrasion, geographic tongue, Fox-Fordyce disease, cutaneous metastatic melanoma and keloids;
wherein the skin damage is selected from skin made atrophic by aging, photodamaged skin, skin damage related to metabolic diseases, skin damage related to steroid use, pressure ulcers/bedsores, and diabetic ulcers.

* * * * *

UNITED STATES PATENT AND TRADEMARK OFFICE
CERTIFICATE OF CORRECTION

PATENT NO. : 11,148,998 B2
APPLICATION NO. : 15/987274
DATED : October 19, 2021
INVENTOR(S) : James Varani et al.

Page 1 of 2

It is certified that error appears in the above-identified patent and that said Letters Patent is hereby corrected as shown below:

In the Claims

Column 54, Claim 1, Line 50-55 reads:

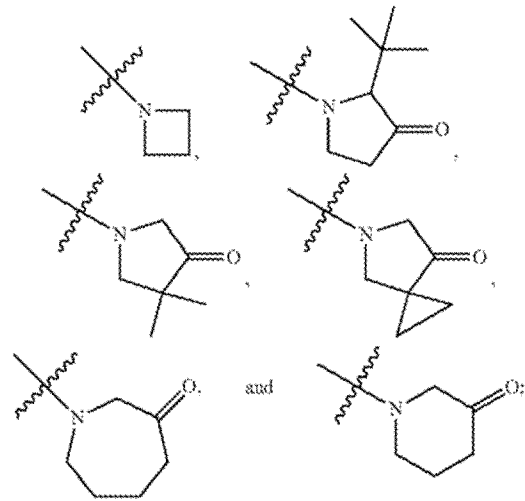

Signed and Sealed this
First Day of November, 2022

Katherine Kelly Vidal
*Director of the United States Patent and Trademark Office*

CERTIFICATE OF CORRECTION (continued)
U.S. Pat. No. 11,148,998 B2

Whereas it should read: